United States Patent [19]

Tischer et al.

[11] Patent Number: 5,194,596
[45] Date of Patent: Mar. 16, 1993

[54] PRODUCTION OF VASCULAR ENDOTHELIAL CELL GROWTH FACTOR

[75] Inventors: Edmund G. Tischer, Palo Alto; Judith A. Abraham, Sunnyvale; John C. Fiddes, Palo Alto; Richard L. Mitchell, Sunnyvale, all of Calif.

[73] Assignee: California Biotechnology Inc., Mountain View, Calif.

[21] Appl. No.: 450,883

[22] Filed: Dec. 14, 1989

Related U.S. Application Data

[63] Continuation-in-part of Ser. No. 387,545, Jul. 27, 1989, abandoned.

[51] Int. Cl.⁵ .................. C07K 3/00; A61K 37/36
[52] U.S. Cl. ................................ 530/399; 530/350
[58] Field of Search ............. 536/27; 435/252.3, 70.1; 530/399, 350

[56] References Cited

PUBLICATIONS

Leung et al Science vol. 246: 1306–1309, Dec. 9, 1989, "Vascular Endothelial Growth Factor is a Secreted Angiogenic Mitogen".

*Primary Examiner*—Christine M. Nucker
*Assistant Examiner*—H. F. Sidberry
*Attorney, Agent, or Firm*—Peter R. Shearer

[57] ABSTRACT

There is described an isolated vascular endothelial cell growth factor selected from the group consisting of bovine vascular endothelial cell growth factor of 120 amino acids and human vascular endothelial cell growth factor of 121 amino acids. The vascular endothelial cell growth factor is useful in the treatment of wounds in which neovascularization or reendothelialization is required for healing.

2 Claims, 9 Drawing Sheets

Sequence

```
            1
1       AAGCTTGAAG TTCATGGACG TCTACCAGCG CNNNNTCTGC CGTCCCATCG AGACCCTGGT
2       AAGCTTGAAG TTTATGGACG TCTACCAGCG CNNNNTCTGC CGTCACATCG AGACCCTGGT
3       AAGCTTGAAG TTCATGGATG TCTACCAGCG CNNNNTCTGC CGTCCCATCG AGACCCTGGT
4       AAGCTTGAAG TTCATGGACG TCTACCAGCG CNNNNTCTGC CGTCCCATCG AGACCCTGGT
5       AAGCTTGAAG TTCATGGATG TCTACCAGCG CAGCTTCTGC CGTCCCATCG AGACCCTGGT

Consensus AAGCTTGAAG TTYATGGAYG TCTACCAGCG CAGCTTCTGC CGTCJCATCG AGACCCTGGT 61
1       GGACATCTTT CAGGAATACC CCGAATTC
2       GGACATCTTT CAGGAGTACC CCGAATTC
3       GGACATCTTC CAGGAATACC CCGAATTC
4       GGACATCTTC CAAGAGTACC CCGAATTC
5       GGATATCTTC CAGGAATACC CCGAATTC Consensus GGAYATCTTY CARGARTACC CCGAATTC
```

The translation of number 5 PCR clone (pET-19A)

```
AAGCTTG AAG TTC ATG GAT GTC TAC CAG CGC AGC TTC TGC CGT CCC ATC
        Lys Phe Met Asp Val Tyr Gln Arg Ser Phe Cys Arg Pro Ile

GAG ACC CTG GTG GAT ATC TTC CAG GAA TAC CCC GAA TTC
Glu Thr Leu Val Asp Ile Phe Gln Glu Tyr Pro
```

FIG.1

```
                                                           7
                                                           TG AAG TTC ATG
Ala Pro Met Ala Glu Gly Gly Gln Lys Pro His Glu Val Val Lys Phe Met

AccI                         50
GAT GTC TAC CAG CGC AGC TTC TGC CGT CCC ATC GAG ACC CTG GTG GAC ATC
Asp Val Tyr Gln Arg Ser Phe Cys Arg Pro Ile Glu Thr Leu Val Asp Ile

100
TTC CAG GAG TAC CCA GAT GAG ATT GAG TTC ATT TTC AAG CCG TCC TGT GTG
Phe Gln Glu Tyr Pro Asp Glu Ile Glu Phe Ile Phe Lys Pro Ser Cys Val

150
CCC CTG ATG CGG TGC GGG GGC TGC TGT AAT GAC GAA AGT CTG GAG TGT GTG
Pro Leu Met Arg Cys Gly Gly Cys Cys Asn Asp Glu Ser Leu Glu Cys Val

200
CCC ACT GAG GAG TTC AAC ATC ACC ATG CAG ATT ATG CGG ATC AAA CCT CAC
Pro Thr Glu Glu Phe Asn Ile Thr Met Gln Ile Met Arg Ile Lys Pro His

250
CAA AGC CAG CAC ATA GGA GAG ATG AGC TTC CTA CAG CAT AAC AAA TGT GAA
Gln Ser Gln His Ile Gly Glu Met Ser Phe Leu Gln His Asn Lys Cys Glu

300
TGC AGA CCA AAG AAA GAT AAA GCA AGG CAA GAA AAA TGT GAC AAG CCG AGG
Cys Arg Pro Lys Lys Asp Lys Ala Arg Gln Glu Lys Cys Asp Lys Pro Arg

326
CGG TGA GCCGGGCTGGAGGAAGGAGCCTCCCTCAGGGTTTCGGGAACCAGACGTCTCACCAGGAA
Arg
AGACTGACACAGAACTACCCATAGCCGCCGCCACCACCACCACACCACCACCACCATCGACAGA
ACAATCCTGAATCCAGAAACCTGACATGAAGGAAGAGGAGGCTGTGCGCAGAGCACTTTGGGTCCGG
AGCGTGAGGCTCCGCAGAAGCATTCATGGGCGGGTGACCCAGCACGGTTCCTCTTGGAATTGGATTG
CCATTTTATTTCTCTTGCTGCTAAATCACCGAGCCCGGAAGATTAGAGAGTTTTATTTCTGGGATTC
CTGTAGACACACCCACCCACATACATACATACATTTATATATATATATATATATTATATATATAAAAAT
AAATATATATATTTTTATATATATATAAAATATATATATTCTTTTAAAAAAAAAAAAAAAAAAAAAA
AAAAA
```

FIG.3a

```
5'                                                                                                              3'
3'                                                                                                              5'
  C ATG GCC CCA ATG GCC GAG GGC CAG AAG CCC CAC GAG GTG GTG AAG TTC ATG GAT GT
    CGG GGT TAC CGG CTC CCG GTC TTC GGG GTG CTC CAC CAC TTC AAG TAC CTA CAG A
(Met)Ala Pro Met Ala Glu Gly Gln Lys Pro His Glu Val Val Lys Phe Met Asp Val Tyr
```

FIG. 3b

Human Platelet Derived Growth Factor A-Chain

CGGATCCG ATGAGGACCTTGGCTTGCCTGCTGCTCCTCGGCTGCGGATACCTCGCCCATGTTCTGGCC
         M  R  T  L  A  C  L  L  L  L  G  C  G  Y  L  A  H  V  L  A

GAGGAAGCCGAGATCCCCCGCGAGGTGATCGAGAGGCTGGCCCGCAGTCAGATCCACAGC
E  E  A  E  I  P  R  E  V  I  E  R  L  A  R  S  Q  I  H  S

ATCCGGGACCTCCAGCGACTCCTGGAGATAGACTCCGTAGGGAGTGAGGATTCTTTGGAC
I  R  D  L  Q  R  L  L  E  I  D  S  V  G  S  E  D  S  L  D

ACCAGCCTGAGAGCTCACGGGGTCCATGCCACTAAGCATGTGCCCGAGAAGCGGCCCCTG
T  S  L  R  A  H  G  V  H  A  T  K  H  V  P  E  K  R  P  L

CCCATTCGGAGGAAGAGAAGCATCGAGGAAGCTGTCCCCGCTGTCTGCAAGACCAGGACG
P  I  R  R  K  R  S  I  E  E  A  V  P  A  V  C  K  T  R  I

GTCATTTACGAGATTCCTCGGAGTCAGGTCGACCCCACGTCCGCCAACTTCCTGATCTGG
V  I  Y  E  I  P  R  S  Q  V  D  P  T  S  A  N  F  L  I  W

CCCCCGTGCGTGGAGGTGAAACGCTGCACCGGCTGCTGCAACACGAGCAGTGTCAAGTGC
P  P  C  V  E  V  K  R  C  T  G  C  C  N  T  S  S  V  K  C

CAGCCCTCCCGCGTCCACCACCGCAGCGTCAAGGTGGCCAAGGTGGAATACGTCAGGAAG
Q  P  S  R  V  H  H  R  S  V  K  V  A  K  V  E  Y  V  R  K

AAGCCAAAATTAAAAGAAGTCCAGGTGAGGTTAGAGGAGCATTTGGAGTGCGCCTGCGCG
K  P  K  L  K  E  V  Q  V  R  L  E  E  H  L  E  C  A  C  A

ACCACAAGCCTGAATCCGGATTATCGGGAAGAGGACACGGGAAGGCCTAGGGAGTCAGGT
T  T  S  L  N  P  D  Y  R  E  E  D  T  G  R  P  R  E  S  G

AAAAAACGGAAAAGAAAAAGGTTAAAACCCACC GGATATCC
K  K  R  K  R  K  L  K  P  T

FIG.4a

Human Platelet Derived Growth Factor B-Chain

```
CGGATCCG  ATGAATCGCTGCTGGGCGCTCTTCCTGTCTCTCTGCTGCTACCTGCGTCTGGTCAGCGCC
          M  N  R  C  W  A  L  F  L  S  L  C  C  Y  L  R  L  V  S  A

GAGGGGGACCCCATTCCCGAGGAGCTTTATGAGATGCTGAGTGACCACTCGATCCGCTCC
          E  G  D  P  I  P  E  E  L  Y  E  M  L  S  D  H  S  I  R  S

TTTGATGATCTCCAACGCCTGCTGCACGGAGACCCCGGAGAGGAAGATGGGGCCGAGTTG
          F  D  D  L  Q  R  L  L  H  G  D  P  G  E  E  D  G  A  E  L

GACCTGAACATGACCCGCTCCCACTCTGGAGGCGAGCTGGAGAGCTTGGCTCGTGGAAGA
          D  L  N  M  T  R  S  H  S  G  G  E  L  E  S  L  A  R  G  R

AGGAGCCTGGGTTCCCTGACCATTGCTGAGCCGGCCATGATCGCCGAGTGCAAGACGCGC
          R  S  L  G  S  L  T  I  A  E  P  A  M  I  A  E  C  K  T  R

ACCGAGGTGTTCGAGATCTCCCGGCGCCTCATAGACCGCACCAACGCCAACTTCCTGGTG
          T  E  V  F  E  I  S  R  R  L  I  D  R  T  N  A  N  F  L  V

TGGCCGCCCTGTGTGGAGGTGCAGCGCTGCTCCGGCTGCTGCAACAACCGCAACGTGCAG
          W  P  P  C  V  E  V  Q  R  C  S  G  C  C  N  N  R  N  V  Q

TGCCGCCCCACCCAGGTGCAGCTGCGACCTGTCCAGGTGAGAAAGATCGAGATTGTGCGG
          C  R  P  T  Q  V  Q  L  R  P  V  Q  V  R  K  I  E  I  V  R

AAGAAGCCAATCTTTAAGAAGGCCACGGTGACGCTGGAAGACCACCTGGCATGCAAGTGT
          K  K  P  I  F  K  K  A  T  V  T  L  E  D  H  L  A  C  K  C

GAGACAGTGGCAGCTGCACGGCCTGTGACCCGAAGCCCGGGGGGTTCCCAGGAGCAGCGA
          E  T  V  A  A  A  R  P  V  T  R  S  P  G  G  S  Q  E  Q  R

GCCAAAACGCCCCAAACTCGGGTGACCATTCGGACGGTGCGAGTCCGCCGGCCCCCCAAG
          A  K  T  P  Q  T  R  V  T  I  R  T  V  R  V  R  R  P  P  K

GGCAAGCACCGGAAATTCAAGCACACGCATGACAAGACGGCACTGAAGGAGACCCTTGGA
          G  K  H  R  K  F  K  H  T  H  D  K  T  A  L  K  E  T  L  G

GCC GGATATCC
          A
```

FIG.4b

```
1
GCA CCC ATG GCA GAA GGA GGG CAG AAA CCC CAC GAA GTG GTG AAG TTC ATG
Ala Pro Met Ala Glu Gly Gly Gln Lys Pro His Glu Val Val Lys Phe Met
1
52
GAT GTC TAC CAG CGC AGC TTC TGC CGT CCC ATC GAG ACC CTG GTG GAC ATC
Asp Val Tyr Gln Arg Ser Phe Cys Arg Pro Ile Glu Thr Leu Val Asp Ile
        20
103
TTC CAG GAG TAC CCA GAT GAG ATT GAG TTC ATT TTC AAG CCG TCC TGT GTG
Phe Gln Glu Tyr Pro Asp Glu Ile Glu Phe Ile Phe Lys Pro Ser Cys Val
                40
154
CCC CTG ATG CGG TGC GGG GGC TGC TGT AAT GAC GAA AGT CTG GAG TGT GTG
Pro Leu Met Arg Cys Gly Gly Cys Cys Asn Asp Glu Ser Leu Glu Cys Val
                                60
205
CCC ACT GAG GAG TTC AAC ATC ACC ATG CAG ATT ATG CGG ATC AAA CCT CAC
Pro Thr Glu Glu Phe Asn Ile Thr Met Gln Ile Met Arg Ile Lys Pro His
                                        80
256
CAA AGC CAG CAC ATA GGA GAG ATG AGC TTC CTA CAG CAT AAC AAA TGT GAA
Gln Ser Gln His Ile Gly Glu Met Ser Phe Leu Gln His Asn Lys Cys Glu
                                                        100
307
TGC AGA CCA AAG AAA GAT AAA GCA AGG CAA GAA AAT CCC TGT GGG CCT TGC
Cys Arg Pro Lys Lys Asp Lys Ala Arg Gln Glu Asn Pro Cys Gly Pro Cys
                        ... ... Arg Gln Glu Ly
358
TCA GAG CGG AGA AAG CAT TTG TTT GTA CAA GAT CCG CAG ACG TGT AAA TGT
Ser Glu Arg Arg Lys His Leu Phe Val Gln Asp Pro Gln Thr Cys Lys Cys
120
409
TCC TGC AAA AAC ACA GAC TCG CGT TGC AAG GCG AGG CAG CTT GAG TTA AAC
Ser Cys Lys Asn Thr Asp Ser Arg Cys Lys Ala Arg Gln Leu Glu Leu Asn
                140
460
GAA CGT ACT TGC AGA TGT GAC AAG CCG AGG CGG TGA GCCGGGCTGGAGGAAGGAG
Glu Arg Thr Cys Arg Cys Asp Lys Pro Arg Arg   .  164
              S Cys Asp Lys Pro Arg Arg   .  120
515
CCTCCCTCAGGGTTTCGGGAACCAGACGTCTCACCAGGAAAGACTGACACAGAACTACCCATAGCCG
582
CCGCCACCACCACCACACCACCACCACCACCATCGACAGAACAATCCTGAATCCAGAAACCTGACAT
649
GAAGGAAGAGGAGGCTGTGCGCAGAGCACTTTGGGTCCGGAGCGTGAGGCTCCGCAGAAGCATTCAT
716
GGGCGGGTGACCCAGCACGGTTCCTCTTGGAATTGGATTGCCATTTTATTTCTCTTGCTGCTAAATC
783
ACCGAGCCCGGAAGATTAGAGAGTTTTATTTCTGGGATTCCTGTAGACACACCCACCCACATACATA
850
CATACATTTATATATATATATATATTATATATATAAAAATAAATATATATATTTTATATATATATAA
917
AATATATATATTCTTTTTAAAAAAAAAAAAAAAAAAAAAAAAAAA
```

FIG.6

```
1                          10
Ala Pro Met Ala Glu Gly Gly Gly Gln Asn His His Glu Val Val Lys Phe
GCA CCC ATG GCA GAA GGA GGA GGG CAG AAT CAT CAC GAA GTG GTG AAG TTC
1
            20                              30
Met Asp Val Tyr Gln Arg Ser Tyr Cys His Pro Ile Glu Thr Leu Val Asp
ATG GAT GTC TAT CAG CGC AGC TAC TGC CAT CCA ATC GAG ACC CTG GTG GAC
52
                    40                                  50
Ile Phe Gln Glu Tyr Pro Asp Glu Ile Glu Tyr Ile Phe Lys Pro Ser Cys
ATC TTC CAG GAG TAC CCT GAT GAG ATC GAG TAC ATC TTC AAG CCA TCC TGT
103
                            60
Val Pro Leu Met Arg Cys Gly Gly Cys Cys Asn Asp Glu Gly Leu Glu Cys
GTG CCC CTG ATG CGA TGC GGG GGC TGC TGC AAT GAC GAG GGC CTG GAG TGT
154
70                                      80
Val Pro Thr Glu Glu Ser Asn Ile Thr Met Gln Ile Met Arg Ile Lys Pro
GTG CCC ACT GAG GAG TCC AAC ATC ACC ATG CAG ATT ATG CGG ATC AAA CCT
205
                    90                                      100
His Gln Gly Gln His Ile Gly Glu Met Ser Phe Leu Gln His Asn Lys Cys
CAC CAA GGC CAG CAC ATA GGA GAG ATG AGC TTC CTA CAG CAC AAC AAA TGT
256
                            110
Glu Cys Arg Pro Lys Lys Asp Arg Ala Arg Gln Glu Asn Pro Cys Gly Pro
GAA TGC AGA CCA AAG AAA GAT AGA GCA AGA CAA GAA AAT CCC TGT GGG CCT
307                                 ... Arg Gln Glu Ly
120                                         130
Cys Ser Glu Arg Arg Lys His Leu Phe Val Gln Asp Pro Gln Thr Cys Lys
TGC TCA GAG CGG AGA AAG CAT TTG TTT GTA CAA GAT CCG CAG ACG TGT AAA
358
            140                                     150
Cys Ser Cys Lys Asn Thr Asp Ser Arg Cys Lys Ala Arg Gln Leu Glu Leu
TGT TCC TGC AAA AAC ACA GAC TCG CGT TGC AAG GCG AGG CAG CTT GAG TTA
409
                    160                 165
Asn Glu Arg Thr Cys Arg Cys Asp Lys Pro Arg Arg
AAC GAA CGT ACT TGC AGA TGT GAC AAG CCG AGG CGG TGA
460             s Cys Asp Lys Pro Arg Arg
                                    121
```

FIG.7

PRODUCTION OF VASCULAR ENDOTHELIAL CELL GROWTH FACTOR

CROSS-REFERENCE TO RELATED APPLICATION

This application is a continuation-in-part of U.S. application Ser. No. 07/387,545 filed Jul. 27, 1989, now abandoned.

BACKGROUND OF THE INVENTION

The invention relates to the field of wound healing. In particular, the invention relates to the production of a wound healing agent that is mitogenic for vascular endothelial cells and consequently is useful in promoting neovascularization (angiogenesis) and reendothelialization of inner vascular surfaces. The invention provides methods and means for producing vascular endothelial cell growth factor by means of recombinant DNA technology.

Angiogenesis, i.e. the growth of new capillary blood vessels, is a process which is crucial to the proper healing of many types of wounds Consequently, factors that are capable of promoting angiogenesis are useful as wound healing agents Angiogenesis is a multi-step process involving capillary endothelial cell proliferation, migration and tissue penetration. A number of known growth factors, including basic and acidic fibroblast growth factor, transforming growth factor alpha and epidermal growth factor, are broadly mitogenic for a variety of cell types as well as being angiogenic and are, therefore, potentially useful in promoting tissue repair. Broad spectrum mitogenicity is desirable in many types of wound healing applications. There are, however, specific types of wound healing applications in which it would be desirable to have a more cell-specific mitogenic activity. For example, following vascular graft surgery, balloon angioplasty or to promote collateral circulation in post-myocardial infarction patients, it would be desirable to employ a wound healing agent incorporating a mitogenic factor having mitogenic activity that is highly specific for vascular endothelial cells since proliferation of other cell types along with endothelial cells could cause blockage and/or reduced blood flow. At present, no highly suitable mitogenic factor is widely available for this type of application.

Recently, a mitogen apparently specific for vascular endothelial cells was isolated from media conditioned by bovine folliculo stellate cells and its partial amino acid sequence determined (Gospodarowicz et al., *PNAS* (1989) 86(19):7311-7315; Ferrara and Henzel, *BBRC* (1989) 161(2):851-858). This factor appears to be a homodimer of two approximately 23 kD subunits. A partially homologous factor that is the mouse homolog of the bovine protein described by Gospodarowicz et al. and Ferarra et al. has also been isolated from the conditioned media of murine AtT20 cells (ATCC CCL 89) and its N-terminal amino acid sequence determined (Plouët et al., *EMBO J.* (1989) 8(12):3801-3806). Both factors have been demonstrated to have mitogenic activity for vascular endothelial cells and for none of the other cell types tested and are therefore useful in a number of types of wound healing applications. Unfortunately, it is not practical and economical to obtain commercial quantities of these factors by purification from their native sources.

SUMMARY OF THE INVENTION

The present invention provides methods and means for obtaining commercial scale quantities of vascular endothelial cell growth factor for use as a wound healing agent. In particular, the present invention provides DNA sequences that encode amino acid sequences of mammalian vascular endothelial cell growth factor. These DNA sequences are inserted into expression vectors under the control of regulatory elements that direct the expression of the encoded amino acid sequences in a suitable expression host. The vascular endothelial cell growth factor expressed in this manner can be recovered and formulated into pharmaceutical compositions that are useful in a variety of wound healing applications in which angiogenesis and/or reendothelialization play an important role.

In the course of providing the DNA sequences herein that encode vascular endothelial cell growth factor, we discovered that two different forms of the coding region are produced in vivo in the mRNA for the factor. These two forms, which apparently arise through alternative message splicing, differ in the length of the open reading frame due to the presence or absence of a 44-codon insert in the mature protein coding region. The predicted higher molecular weight factor, comprising a 164-amino acid sequence in the bovine case and a 165-amino acid sequence in the human case, is believed to correspond to the approximately 23-kD subunit isolated by Gospodarowicz et al. (supra) and by Ferrara and Henzel (supra). The novel, lower molecular weight factor predicted from the coding region lacking the insert comprises a 120-amino acid sequence in the bovine case and 121-amino acid sequence in the human case. The lower molecular weight form differs not only in the length of the amino acid sequence, but also in the presence of a Lys residue at position 114 in the bovine protein (position 115 in the human protein) that is not present in the higher molecular weight form because of the differential message splicing which occurs within the corresponding codon at this position. For convenience, these two forms of vascular endothelial cell growth factor will be referred to, respectively, as $bVEGF_{164}$ and $bVEGF_{120}$ for the bovine factor ($hVEGF_{165}$ and $hVEGF_{121}$ for the human factor).

Surprisingly, the amino acid sequence deduced from N-terminal sequence analysis and an isolated DNA sequence (shown in FIG. 3a) indicates a significant level of sequence homology between bovine vascular endothelial cell growth factor and corresponding sequences from each of the A-chain and B-chain subunits of human platelet-derived growth factor (PDGF), with complete conservation of eight cysteine residues among the mature forms of all three sequences. Accordingly, hybrid dimeric proteins can be prepared comprising a first polypeptide chain and a second polypeptide chain, wherein one of the chains comprises at least a portion of the amino acid sequence of the A-chain or the B-chain subunit of platelet-derived growth factor and the other chain comprises at least a portion of the amino acid sequence of vascular endothelial cell growth factor. Preparation of the hybrid proteins allows one to "tailor" the properties of the molecule such that the hybrid exhibits a profile of mitogenic activity between that of vascular endothelial cell growth factor and platelet-derived growth factor. The PDGF B—B homodimer is mitogenic for vascular smooth muscle cells but not for vascular endothelial cells. Conversely, the vascular endothelial cell growth factor of the present invention has the opposite specificity. A hybrid factor may stimulate both cell types and therefore be useful as a broader-spectrum mitogen in wound healing therapies.

BRIEF DESCRIPTION OF THE DRAWINGS

FIG. 1 is a representation of five DNA sequences generated by a modification of the polymerase chain reaction process. One of the five (pET-19A; clone no. 5) encodes amino acids no. 15 to 38 of the mature, sequenced form of bovine vascular endothelial cell growth factor. The figure also includes a consensus DNA sequence derived from the five DNA sequences, as well as a translation of pET-19A. Each sequence includes DNA linkers at either end which represent an EcoRI restriction site and a HindIII restriction site.

FIG. 3a is a representation of a DNA sequence, as well as its deduced amino acid sequence, derived from a clone, designated 11B'. The illustrated sequence encodes amino acids no. 15 to 120 of bovine vascular endothelial cell growth factor (bVEGF$_{120}$).

FIG. 3b is a representation of a synthetic DNA sequence, based on preferred codon usage in human cells, which encodes amino acids no. 1 to 19 of bVEGF$_{120}$ and which overlaps the 5' end of the DNA sequence of FIG. 3a. This synthetic DNA can be enzymatically joined to the isolated DNA sequence of FIG. 3a, after the DNA sequence in FIG. 3a has been digested with the restriction enzyme AccI, to produce a DNA sequence encoding the full length, mature bVEGF$_{120}$ protein.

FIG. 4 is a representation of isolated DNA sequences encoding the A-chain and B-chain subunits of human platelet-derived growth factor, and the amino acid sequences of the precursors of these two proteins as deduced from the DNA sequences.

FIG. 6 is a representation of the isolated cDNA sequences encoding bVEGF$_{120}$ and bVEGF$_{164}$. The boxed DNA sequence beginning at base 342 represents the insert sequence that is present in the alternatively spliced cDNA which encodes bVEGF$_{164}$. The amino acid sequence given immediately below the nucleotide sequence represents the deduced sequence for bVEGF$_{164}$. The deduced amino acid sequence for bVEGF$_{120}$ is identical to that of bVEGF$_{164}$ through position 113 (Glu). The carboxyl-terminal sequence of bVEGF$_{120}$, beginning at position 111 (Arg) is given in italics below the bVEGF$_{164}$ sequence in FIG. 6.

FIG. 7 is a representation of the native human DNA sequences encoding hVEGF$_{121}$ and hVEGF$_{165}$. The DNA sequences shown represent composites of sequences obtained from human genomic and human cDNA clones. The bracketed amino acid (Gly) encoded by codon 7 represents an inserted amino acid relative to the sequences of bVEGF$_{120}$ and bVEGF$_{164}$.

DETAILED DESCRIPTION OF THE INVENTION

Figure 2:
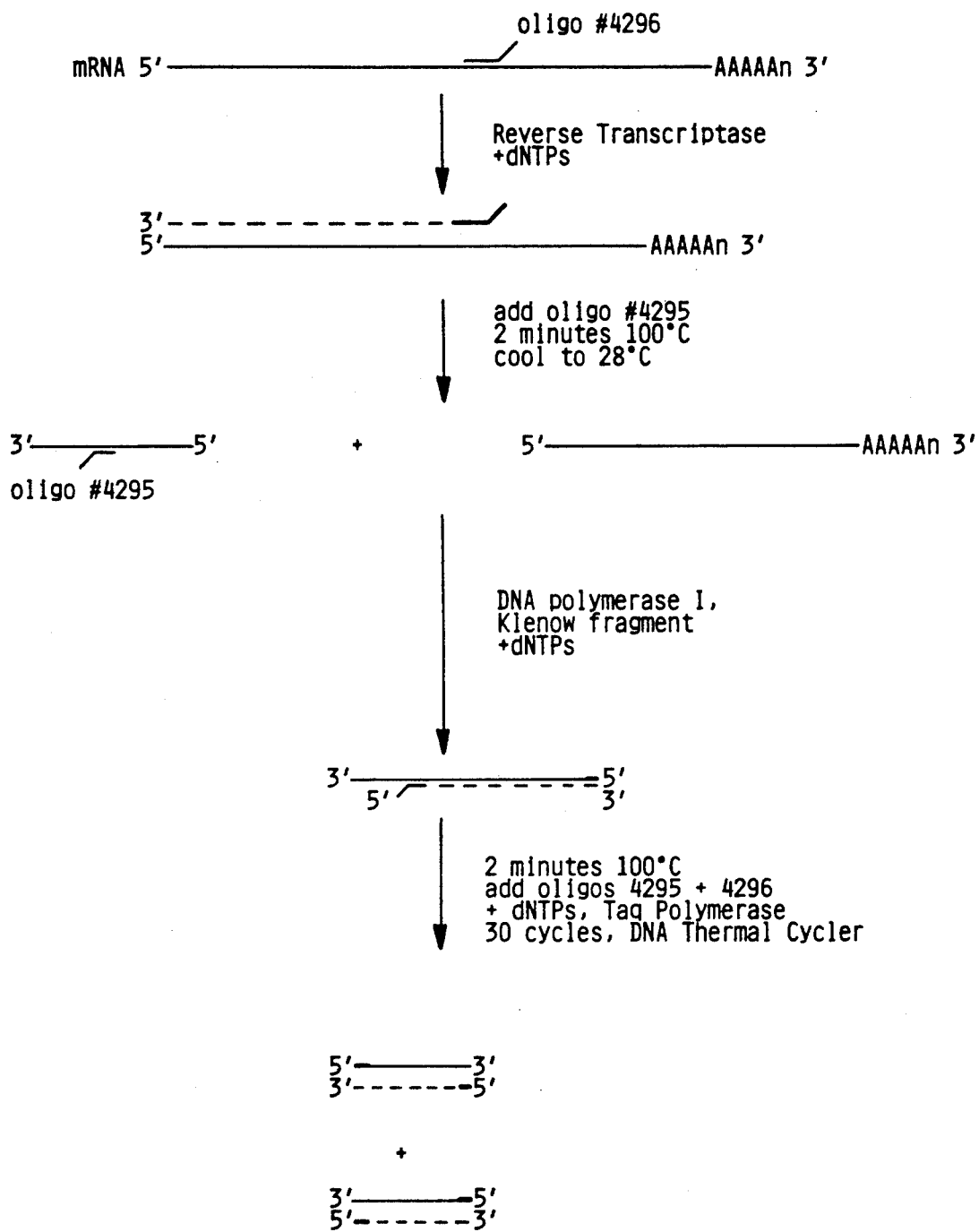
FIG. 2 is a schematic representation of the method by which the five DNAs of FIG. 1 were generated and amplified from bovine folliculo stellate cell mRNA.

As used herein, the term "vascular endothelial cell growth factor" refers to a mammalian protein that has mitogenic activity for vascular endothelial cells and that:

(a) has an amino acid sequence which either is encoded by a DNA sequence that is capable of hybridizing, under standard hybridization conditions, to the DNA sequence shown in FIG. 3a; or (b) is substantially homologous to the amino acid sequence of bVEGF$_{120}$, bVEGF$_{164}$, hVEGF$_{121}$ or hVEGF$_{165}$, shown in FIG. 6 and FIG. 7.

An amino acid sequence is considered to be "substantially homologous" herein if the level of amino acid sequence homology is at least 50% and, preferably at least 80%, compared with the protein in question. "Standard hybridization conditions", as used herein means the use of 40% Formamide Buffer (described below) as the prehybridization/hybridization buffer and washing in 1×SSC, 0.1% SDS at 50° C.

The amino acid sequence numbering system used herein for vascular endothelial cell growth factor is based on the mature forms of the protein, i.e. the post-translationally processed forms. Accordingly, the residue numbered one in the bovine or human proteins is alanine, which is the first residue of the isolated, mature forms of these proteins.

Mitogenic activity for vascular endothelial cells can be determined by an assay which uses, as target cells, adrenal cortex-derived capillary endothelial cells (ACE cells). This assay is carried out essentially as described in Gospodarowicz et al., *J. Cell Physiol.* (1986) 127:121–136, the disclosure of which is incorporated herein by reference. Generally, stock cultures of ACE cells are maintained in the presence of Dulbecco's modified Eagle's medium (DMEM-21) supplemented with 10% calf serum. The antibiotics penicillin (50 IU/ml), streptomycin (50 μg/ml), gentamycin (50 μg/ml), and Fungizone (0.25 μg/ml) and 2 mM L-glutamine can also be added to the medium. Cells are passaged weekly on tissue culture dishes at a split ratio of between 1:40 and 1:200 (the preferred split ratio is that which gives 2.5×10$^5$ cells in 15 ml of medium in T75 flasks). For the mitogenic assay, cells are seeded in 12 well cluster plates at a density of 5×10$^3$ cells per well in 1 ml Dulbecco's modified Eagle's medium supplemented with 10% calf serum and antibiotics as described in Gospodarowicz et al., *Europ. J. Cell. Biol.* (1988) 46:144–151. Alternatively, the ACE cells are plated in 35 mm dishes or 6 well cluster plates at a density of 5–10×10$^3$ cells per dish or well in 2 ml of medium as described in Gospodarowicz, et al., *J. Cell Physiol.* (1986) 127:121–136. Ten-microliter aliquots of appropriate dilutions of each sample are then added to duplicate or triplicate wells in the dishes on days 0 and 2. After 4 or 5 days in culture, the plates are trypsinized and cell densities determined in a Coulter counter. For purposes of description herein, a factor is considered to have mitogenic activity for vascular endothelial cells if the cell density at the end of this assay is at least 1.5 times and preferably at least 3 times the cell density of control wells receiving no factor additions.

Although the DNA sequence illustrated in FIG. 3a was obtained from a bovine cell cDNA library, and therefore represents a sequence which encodes a bovine protein, the DNA sequence provided allows for the retrieval of sequences encoding homologous proteins from other mammalian species. Accordingly, we have employed the illustrated bovine sequence as a probe to retrieve DNA sequences encoding the corresponding human proteins.

Also included within the scope of "vascular endothelial cell growth factor" herein are biologically active fragments thereof, as well as N-terminally or C-terminally extended versions thereof or analogs thereof substituting and/or deleting or inserting one or more amino acid residues which retain qualitatively the biological activities of the protein described herein. While the native form of the bovine vascular endothelial cell growth factor described herein is apparently glycosylated, there is currently no evidence that glycosylation is essential for biological activity. Accordingly, biologically active nonglycosylated or partially glycosylated forms, which will be produced by prokaryotic or eukaryotic hosts using the expression sequences provided herein, are included within the scope of "vascular endothelial cell growth factor".

Vascular endothelial cell growth factor—as isolated by Gospodarowicz et al. (supra) and by Ferrara and Henzel (supra)—is a dimeric protein of approximately 45–46 kD, as determined by SDS polyacrylamide gel electrophoresis. Bovine vascular endothelial cell growth factor was obtained in homogeneous form from cell culture media conditioned by folliculo stellate cells, by a process which involved the steps of ammonium sulfate precipitation; heparin-Sepharose affinity chromatography; size-exclusion gel chromatography; cation exchange chromatography; and reverse phase high performance liquid chromatography. Similar procedures may be employed to purify a corresponding protein from conditioned media of cultured cells from other mammalian species which are known to produce vascular endothelial cell growth factor, for example, murine AtT20 cells. We have also determined, by Northern blot analyses, that human fetal vascular smooth muscle cells are a good source of human vascular endothelial cell growth factor and mRNA encoding the factor.

Isolated bovine vascular endothelial cell growth factor obtained as described above was sequenced using the Edman degradation technique on an automated gas-phase protein sequenator. A single major 24-amino acid N-terminal sequence was obtained, indicating that the protein is homodimeric. Following tryptic digestion of the protein and amino acid sequencing of various peptide fragments, it was determined, according to overlapping amino acid sequences, that the bovine protein has the following 41-amino acid N-terminal sequence*:

APMAEGGQKPHEVVKFMDVYQRSFCRPIET
LVDIFQEYPDE (*Using the standard single letter abbreviation code for amino acids)

Using the N-terminal amino acid sequence for bovine vascular endothelial cell growth factor described above, a number of unsuccessful efforts were made to retrieve a full or partial length cDNA encoding the protein by probing a folliculo stellate cell cDNA library using degenerate oligonucleotide probe mixtures encoding portions of the amino acid sequence. The DNA segment of FIG. 3a was ultimately retrieved from the cDNA library using a probe generated by amplifying that portion of the nucleotide sequence encoding amino acids 15 to 38 (and two-thirds of the codon for amino acid 39) by a modification of the polymerase chain reaction method. The polymerase chain reaction method for amplifying a desired DNA sequence is described in detail in U.S. Pat. Nos. 4,683,202 and 4,683,195, the disclosures of which are incorporated herein by reference. The procedure allows the amplification of a desired nucleotide sequence, even if the bulk of the sequence is not known, provided one is able to provide oligonucleotide primers that will hybridize to either end of the sequence that it is desired to amplify. The polymerase chain reaction process has been employed to amplify a desired segment of cDNA using degenerate oligonucleotides as primers (Lee et al., Science (1988) (1288–1291)).

The DNA probe used to retrieve the cDNA of FIG. 3a was selected from the five homologous sequences shown in FIG. 1. These sequences were obtained by a procedure which is illustrated schematically in FIG. 2 and which is described in greater detail in the examples which follow. In accordance with the illustrated procedure, poly(A)+RNA from bovine folliculo stellate cells was precipitated with an anti-sense primer consisting of a 16-fold degenerate synthetic oligonucleotide mixture based on the amino acid sequence of amino acids no. 35 to 39 of bovine vascular endothelial cell growth factor. The 24-base oligonucleotide primer consisted of 14 bases reflecting the amino acid sequence, with a 10-base EcoRI linker on the 5' end. The oligonucleotide primer sequences in the mixture which hybridized to the poly(A)+ RNA served to prime the synthesis of a DNA strand complementary to a section of the desired mRNA in the presence of deoxynucleotide triphosphates (dNTPs) and reverse transcriptase. A second DNA strand, complementary to the first synthesized strand, was then prepared by hybridizing the first synthesized strand to a sense-strand primer consisting of an 8-fold degenerate synthetic 24-base oligonucleotide mixture based on the amino acid sequence of amino acids no. 15 to 19 of bovine vascular endothelial cell growth factor. The second strand oligonucleotide primer contained a 14-base region reflecting the amino acid sequence, joined to a 10-base HindIII linker on the 5' end. The oligonucleotide primer sequences in the mixture which hybridized to the first synthesized DNA strand served to prime the synthesis of a second DNA strand in the presence of dNTPs and DNA polymerase I, Klenow fragment. Since the 10 base linker sequence in the primer could not hybridize to the first strand DNA, second strand synthesis was carried out at a temperature, i.e. 28° C., at which the remaining 14 nucleotides could be expected to remain hybridized to the first strand DNA. DNA polymerase I, Klenow fragment, was used for the second strand synthesis, since Thermus aquaticus (Taq) DNA polymerase, which is normally used in the polymerase chain reaction, would not be effective to catalyze DNA synthesis at this temperature. Second strand synthesis produced a sense strand coding for that portion of bovine vascular endothelial cell growth factor extending from amino acid no. 15 to amino acid no. 38 (and including two-thirds of the codon for amino acid 39).

The two synthesized DNA strands were then separated and the desired sequence was amplified by a repeated sequence of reactions in which the single stranded DNAs were used as templates for the synthesis of complementary strands in the presence of both the sense- and anti-sense oligonucleotide primer mixtures and Thermus aquaticus (Taq) DNA polymerase. After each synthesis of complementary strands, the reaction mixture was heated to separate the strands and the reaction was repeated.

Figure 5:
FIG. 5 is a photograph of an ethidium bromide stained polyacrylamide gel containing DNA produced by amplification of a portion of the mRNA encoding bovine vascular endothelial cell growth factor.

After 30 cycles of amplification, the DNA from the polymerase chain reaction mixture was subjected to electrophoresis on a 6% polyacrylamide gel. The DNA in the gel was stained with ethidium bromide and the band having the appropriate size for the coding sequence for amino acids 15 to 38 (and two-thirds of the codon for amino acid 39) together with the HindIII and EcoRI linkers from the priming oligonucleotides was cut from the gel. The ethidium bromide stained gel is shown in the photograph of FIG. 5, where the dominant band representing the desired amplified sequence can be clearly visualized. DNA was electroeluted from the excised gel fragment containing the dominant band, digested with HindIII and EcoRI and ligated into HindIII- and EcoRI-cut M13mp19 and M13mp18 phage vectors. DNA sequence analysis of white plaques isolated after transformation of the ligation mixtures into E. coli JM103 host cells demonstrated that a cDNA sequence encoding amino acids 15 to 38 (and containing two-thirds of the codon for amino acid 39) of vascular endothelial cell growth factor indeed had been obtained. The amplified DNA sequence contained in one of these recombinant phage (pET-19A) was employed as a probe to retrieve a cloned cDNA sequence from a bovine folliculo stellate cell cDNA library. The isolated cloned sequence consisted of an 797-base pair insert coding for all but the 14 N-terminal amino acids of one of the mature forms of bovine vascular endothelial cell growth factor. The isolated cloned insert was ligated into the EcoRI site of pUC8 to create the plasmid designated pST800. The insert contained the nucleotide sequence shown in FIG. 3a (in FIG. 3a, the EcoRI linkers on each end of the insert are not shown; hence the sequence is numbered beginning with nucleotide 7 of the insert). The coding region of amino acids no. 15 to 120 of bVEGF$_{120}$ is represented by nucleotides no. 9 to 326 of FIG. 3a.

The amino acid sequence predicted from the isolated DNA sequence shown in FIG. 3a contains one potential site for N-linked glycosylation at the asparagine residue at amino acid no. 74. Since an N-linked glycosylation of approximately 3 kD at this site would predict a total molecular weight of about 17 kD for the encoded protein, which is considerably smaller than the apparent molecular weight of 23 kD observed for the vascular endothelial cell growth factor subunits isolated by Gospodarowicz et al. and by Ferrara and Henzel, it is apparent that the isolated cDNA encodes a different form of vascular endothelial cell growth factor than that previously observed. A polymerase chain reaction experiment indicated that alternative forms of the vascular endothelial cell growth factor coding region exist.

A polymerase chain reaction was primed from folliculo stellate poly(A)+ RNA using a sense oligonucleotide corresponding to bases 70-126 in FIG. 6, and an antisense oligonucleotide corresponding to bases 513-572. Polyacrylamide gel analysis of the products after digestion with BstNI (which cuts within each of the primers) revealed two major species of approximately 300 and 450 bp. Both of these products were subcloned into M13 vectors and sequenced. The DNA sequence of the smaller product (311 bp) corresponded to that predicted if the PCR amplified the cDNA sequence carried in pST800. The sequence of the larger fragment was identical to that of the 311 bp product, except for an insert of 132 bp (boxed sequence in FIG. 6). Analysis of human vascular endothelial cell growth factor genomic clones, obtained as described below, has indicated that this insert occurs at an exon-intron junction, suggesting that the two forms of the coding region arise through alternative exon splicing.

The DNA sequences shown in FIG. 1 or FIG. 3a are useful in the retrieval of DNA coding for full length bovine vascular endothelial cell growth factor, or for the corresponding vascular endothelial cell growth factor of other species, including the corresponding human protein, or for related proteins in the same gene family as vascular endothelial cell growth factor.

To obtain bovine vascular endothelial cell growth factor cDNA clones containing sequence information upstream from that present in pST800 (FIG. 3a), we employed a modification of the "RACE" polymerase chain reaction technique described by Frohman, M. A. et al., PNAS (USA) (1988) 85;8998-9002. A linker was ligated onto the 5' end of the duplex resulting from primer extension of the vascular endothelial cell growth factor mRNA, after which polymerase chain reaction was carried out using as primers the original primer-extension oligonucleotide and an oligonucleotide complementary to the linker. Sequence analysis of the resulting polymerase chain reaction products, after digestion of the primers with HindIII and subcloning into M13 vectors, gave sequences encoding the mature amino terminus of vascular endothelial cell growth factor (FIG. 6). The longest cDNA clone obtained extended 14 bp 5' to the beginning of the mature protein coding region (AGTGGTCCCAGGCTGCACCC ... ), revealing four additional amino acids of the vascular endothelial cell growth factor precursor (WSQAAPMA ... ).

In order to retrieve DNA sequences for the human forms of vascular endothelial cell growth factor, the sequences in FIG. 1, FIG. 3a, or FIG. 6, preferably the sequences of FIG. 3a or FIG. 6 or segments thereof, are used as probes to retrieve the desired sequences from cDNA or genomic libraries. Genomic libraries can be prepared by known techniques and are now widely commercially available. A suitable genomic DNA library from which genomic DNA sequences encoding human vascular endothelial cell growth factor can be isolated is a human fibroblast genomic library (Stratagene Inc., La Jolla, Calif.). This library, obtained from the W138 cell line, harbors >15 kb DNA inserts in the Lambda FIX TM vector. Alternatively, a genomic library can be prepared by the technique disclosed by Frischauf, A. M. in Methods in Enzymology, eds. Berger, S. L. and Kimmel, A. R., Vol. 152, pp. 190-199 (1987) Academic Press, N.Y. Methods for preparing cDNA libraries are also well known to those skilled in the art (see, e.g., Kimmel, A. R. and Berger, S. L., ibid., pp. 307-316). Preferably, the cDNA library is prepared from a cell line or tissue source which actively produces vascular endothelial cell growth factor. For the isolation of a cDNA sequence encoding the human protein, it is preferred to employ a cDNA library prepared from fetal human vascular smooth muscle cells. A DNA sequence encoding vascular endothelial cell growth factor, which is obtained as described above, is inserted into a suitable expression vector under the control of regulatory sequences capable of directing expression of the DNA sequence in a desired host. If the DNA sequence retrieved is a genomic sequence containing introns, then it is desirable to insert the sequence into an expression vector that is compatible with a eukaryotic host. Expression of the genomic DNA encoding vascular endothelial cell growth factor in a eukaryotic host is accompanied by correct splicing of the encoded RNA to remove intron sequences, thereby producing an mRNA template encoding the desired protein. Alternatively, a synthetic DNA sequence can be constructed from synthetic oligonucleotides that represents the coding sequence obtained after the intron sequences in the genomic clone have been removed. Expression vectors containing this synthetic sequence or the cDNA sequence encoding vascular endothelial cell growth factor can be used to express the protein in prokaryotic or eukaryotic hosts. Exemplary control sequence DNAs and hosts are described below under Standard Procedures.

Biologically active vascular endothelial cell growth factor is produced in accordance with the teachings of this invention, as a homodimeric molecule. A fully active protein is produced by expression and/or recovery of the polypeptide sequence encoded by the DNA sequence of the invention under conditions which allow the formation of disulfide bonds in order to form a dimer.

The present invention also provides for the production of chimeric, dimeric proteins in which a portion of the primary amino acid structure corresponds to a portion of either the A-chain subunit or the B-chain subunit of platelet-derived growth factor and a portion of the primary amino acid structure corresponds to a portion of vascular endothelial cell growth factor. In particular, there is provided a chimeric growth factor comprising a first polypeptide chain and a second polypeptide chain, said chains being disulfide linked, wherein the first polypeptide chain comprises at least a portion of the amino acid sequence of either the A-chain subunit or the B-chain subunit of platelet-derived growth factor and the second chain comprises at least a portion of the amino acid sequence of vascular endothelial cell growth factor.

Platelet-derived growth factor is an approximately 30 kD dimer which has been isolated in both homodimeric and heterodimeric forms. Platelet-derived growth factor heterodimer contains two polypeptide chains, designated the A- and B-chains. The mature A- and B-chains exhibit approximately 40% amino acid sequence homology, with complete conservation of eight cysteine residues. Platelet-derived growth factor exists in vivo as either an A-A or a B-B homodimer or as an A-B heterodimer.

DNA sequences encoding the A-chain and B-chain subunits of platelet-derived growth factor have been isolated and sequenced (A-chain cDNA (human) is disclosed in Betsholtz, C., et al., *Nature* (1986) 320; A-chain genomic DNA (human) in Bonthron, D. T., et al., *PNAS* (1988) 85:1496; B-chain cDNA (human) in Collins, T., et al., *Nature* (1985) 316:748; and B-chain genomic DNA (human) in Chin, I.-M., et al., *Cell* (1984) 37:123). FIG. 4 illustrates the isolated cDNA sequences and deduced precursor amino acid sequences for the A- and B-chain subunits of human platelet-derived derived growth factor with a BamHI linker joined to the 5' end and an EcoRV linker joined to the 3' end of the cDNAs each case. Each of these sequences can be inserted into a suitable expression vector under the control of appropriate regulatory elements and expressed in a suitable host, such as for example, *E. coli* or a eukaryotic host such as Chinese hamster ovary (CHO) cells or yeast.

Examples of the chimeric growth factor proteins contemplated by the present invention include: a dimeric protein consisting of the full length A-chain subunit of platelet-derived growth factor linked by disulfide bonds to a full length vascular endothelial cell growth factor polypeptide chain; and a dimeric protein consisting of the full length B-chain subunit of platelet-derived growth factor linked by disulfide bonds to a full length vascular endothelial cell growth factor polypeptide chain. In other, less preferred embodiments, the dimeric protein can consist of two disulfide-linked polypeptide chains in which one or both of the chains consists of an N-terminal segment having an amino acid sequence corresponding to an N-terminal portion of either the A- or B-chain subunit of platelet-derived growth factor or vascular endothelial cell growth factor and a C-terminal segment corresponding to a C-terminal sequence selected from one of the other two chains. For example, one can prepare a dimer in which one polypeptide chain consists of the N-terminal one-half of the A-chain of platelet-derived growth factor linked through a peptide bond to the C-terminal one-half of vascular endothelial cell growth factor; and the other polypeptide chain consists of the entire amino acid sequence of vascular endothelial cell growth factor. Conversely, one of the polypeptide chains can be composed of an N-terminal portion of vascular endothelial cell growth factor linked to a C-terminal segment of the A- or B-chain subunit of platelet-derived growth factor and the other polypeptide chain can have the amino acid sequence of vascular endothelial cell growth factor. Numerous different hybrid combinations can be prepared, as will be readily apparent.

In order to prepare the chimeric growth factors of the invention, a DNA sequence encoding each desired chain is inserted into a suitable expression vector, e.g. a plasmid, under the control of regulatory sequences capable of directing its expression in a host cell. Host cells are then transformed with the expression vectors. If desired, a single host may be cotransformed with expression vectors for each of the two chains. Alternatively, separate host cells can be transformed with the vectors encoding the two polypeptide chains. The polypeptide chains are then expressed and recovered in a conventional manner. If the polypeptide chains are expressed with secretion signal sequences such that they are secreted from host cells, they may naturally form the correct dimer structure during synthesis and secretion. The dimers may then be purified using the techniques described in Gospodarowicz et al., *PNAS* (1989) 86(19):7311–7316 and Ferrara and Henzel, *BBRC* (1989) 61(2):851–858. If the correct dimer structure is not obtained by this route, or if the two chains of the chimera are synthesized in different hosts, then an example of one means of refolding and dimerizing the chains would be to treat the partially-purified or purified chains with guanidine-HCl, $Na_2SO_3$ and $Na_2S_4O_6$, as described in more detail in the examples below. The resulting S-sulfonated, denatured proteins are then refolded and dimerized together in the presence of 5 mM glutathione, 0.5 mM glutathione disulfide and urea before final purification.

COMPOSITIONS AND USES

Vascular endothelial cell growth factor ($bVEGF_{120}$, $bVEGF_{164}$, $hVEGF_{121}$ or $hVEGF_{165}$) provided by the invention is useful as a wound healing agent, particularly in applications where it is desired to re-endothelialize vascular tissue, or where the growth of a new capillary bed (angiogenesis) is important.

Vascular endothelial cell growth factor can, therefore, be used in the treatment of full-thickness wounds such as dermal ulcers, including the categories of pressure sores, venous ulcers and diabetic ulcers. In addition, vascular endothelial cell growth factor can be used in the treatment of full-thickness burns and injuries where angiogenesis is required to prepare the burn or injured site for a skin graft or flap. In this case, the vascular endothelial cell growth factor is either applied directly to the site or it is used to soak the skin or flap that is being transplanted prior to grafting. In a similar fashion, vascular endothelial cell growth factor can be used in plastic surgery when reconstruction is required following a burn, other trauma or for cosmetic purposes.

Angiogenesis is also important in keeping wounds clean and non-infected. Vascular endothelial cell growth factor can, therefore, be used in association with general surgery and following the repair of cuts and lacerations. It is particularly useful in the treatment of abdominal wounds with a high risk of infection. Neovascularization is also key to fracture repair since blood vessels develop at the site of bone injury. Administration of vascular endothelial cell growth factor to the site of a fracture is, therefore, another utility.

In cases where vascular endothelial cell growth factor is being used for topical wound healing, as described above, it may be administered by any of the routes described below for the re-endothelialization of vascular tissue, or more preferably by topical means. In these cases, it will be administered as either a solution, spray, gel, cream, ointment or as a dry powder directly to the site of injury. Slow release devices directing vascular endothelial cell growth factor to the injured site will also be used. In topical applications, vascular endothelial cell growth factor will be applied at a concentration ranging from 50 to 1,000 µg/ml either in a single application, or in dosing regimens that are daily or every few days for a period of one to several weeks. Generally, the amount of topical formulation administered is that which is sufficient to apply from about 0.1 to 100 µg/cm$^2$ of vascular endothelial cell growth factor, based on the surface area of the wound.

Vascular endothelial cell growth factor can be used as a post-operative wound healing agent in balloon angioplasty, a procedure in which vascular endothelial cells are removed or damaged, together with compression of atherosclerotic plaques. Vascular endothelial cell growth factor can be applied to inner vascular surfaces by systemic or local intravenous application either as intravenous bolus injection or infusions. If desired, the vascular endothelial cell growth factor can be administered over time using a micrometering pump. Suitable compositions for intravenous administration comprise vascular endothelial cell growth factor in an amount effective to promote endothelial cell growth and a parenteral carrier material. The vascular endothelial cell growth factor can be present in the composition over a wide range of concentration, for example, from about 50 µg/ml to about 1,000 µg/ml using injections of 3 to 10 ml per patient, administered once or in dosing regimens that allow for multiple applications. Any of the known parenteral carrier vehicles can be used, such as normal saline or 5-10% dextrose.

Vascular endothelial cell growth factor can also be used to promote endothelialization in vascular graft surgery. In the case of vascular grafts using either transplanted vessels or synthetic material, for example, vascular endothelial cell growth factor can be applied to the surfaces of the graft and/or at the junctions of the graft and the existing vasculature in order to promote the growth of vascular endothelial cells. For such applications, the vascular endothelial cell growth factor can be applied intravenously as described above for balloon angioplasty or it can be applied directly to the surfaces of the graft and/or the existing vasculature either before or during surgery. In such cases, it may be desired to apply the vascular endothelial cell growth factor in a thickened carrier material so that it will adhere to the affected surface. Suitable carrier materials include, for example, 1-5% carbopol. The vascular endothelial cell growth factor can be present in the carrier over a wide range of concentrations, for example, from about 50 µg/mg to about 1,000 µg/mg. Alternatively, the vascular endothelial cell growth factor can be delivered to the site by a micrometering pump as a parenteral solution.

Vascular endothelial cell growth factor can also be employed to repair vascular damage following myocardial infarction and to circumvent the need for coronary bypass surgery by stimulating the growth of a collateral circulation. The vascular endothelial cell growth factor is administered intravenously for this purpose, either in individual injections or by micrometering pump over a period of time as described above or by direct infusion or injection to the site of damaged cardiac muscle.

Vascular endothelial cell growth factor can also be used as a growth factor for the in vitro culturing of endothelial cells. For such uses, vascular endothelial cell growth factor can be added to the cell culture medium at a concentration from about 10 pg/ml to about 10 ng/ml.

The hybrid growth factor molecules of the invention will be expected to exhibit mitogenic profiles falling between those of platelet-derived growth factor and vascular endothelial cell growth factor. The most pronounced distinction between the activities of the two factors is that platelet-derived growth factor exhibits substantial mitogenic activity on smooth muscle cells and fibroblasts, but not on endothelial cells, whereas vascular endothelial cell growth factor exhibits the opposite specificity. The mitogenic activity of PDGF A- and/or B-chain on smooth muscles cells and fibroblasts tends to impart tensile strength to a healing wound. Therefore, the growth factor which is a hybrid between platelet-derived growth factor and vascular endothelial cell growth factor can be applied to a wound in order to induce neovascularization and impart tensile strength to the wound area during and after healing. The hybrid growth factors are applied in essentially the same manner and at the same dosages as described above for vascular endothelial cell growth factor.

STANDARD PROCEDURES

Most of the procedures which are used to transform cells, construct vectors, extract messenger RNA, prepare cDNA libraries, and the like are widely practiced in the art and most practitioners are familiar with the standard resource materials which describe specific conditions and procedures. However, for convenience, the following paragraphs may serve as a guideline.

HOSTS AND CONTROL SEQUENCES

Both prokaryotic and eukaryotic systems may be used to express the vascular endothelial cell growth factor encoding sequences: prokaryotic hosts are, of course, the most convenient for cloning procedures. Prokaryotes most frequently are represented by various strains of E. coli; however, other microbial strains may also be used. Plasmid vectors which contain replication sites, selectable markers and control sequences derived from a species compatible with the microbial host are used; for example, E. coli is typically transformed using derivatives of pBR322, a plasmid constructed from parts of three naturally-occurring plasmids, two obtained from species of Salmonella, and one isolated from E. coli by Bolivar, et al., Gene (1977) 2:95. pBR322 contains genes for ampicillin and tetracycline resistance, and thus provides multiple selectable markers which can be either retained or destroyed in constructing the desired vector. Commonly used prokaryotic control sequences (also referred to herein as "regulatory elements") which are defined herein to include promoters for transcription initiation, optionally with an operator, along with ribosome binding site sequences, include such commonly used promoters as the beta-lactamase (penicillinase) and lactose (lac) promoter systems (Chang, et al., Nature (1977) 198:1056) and the tryptophan (trp) promoter system (Goeddel, et al., Nucleic Acids Res. (1980) 8:4057 and the lambda derived $P_L$ promoter and N-gene ribosome binding site (Shimatake, et al., Nature (1981) 292:128).

In addition to bacteria, eucaryotic microbes, such as yeast may also be used as hosts. Laboratory strains of Saccharomyces cerevisiae, Baker's yeast, are most used although a number of other stains or species are commonly available. Vectors employing, for example, the 2 μ origin of replication of Broach, J. R., Meth. Enz. (1983) 101:307, or other yeast compatible origins of replication (see, for example, Stinchcomb, et al., Nature (1979) 282:39, Tschumper, G., et al., Gene (1980) 10:157 and Clarke, L. et al., Meth. Enz. (1983) 101:300) may be used. Control sequences for yeast vectors include promoters for the synthesis of glycolytic enzymes (Hess, et al., J. Adv. Enzyme Req. (1968) 7:149; Holland, et al., Biochemistry (1978) 17:4900). Additional promoters known in the art include the promoter for 3-phosphoglycerate kinase (Hitzeman, et al., J. Biol. Chem. (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeastderived genes.

It is also, of course, possible to express genes encoding polypeptides in eukaryotic host cell cultures derived from multicellular organisms. See, for example, Axel, et al. U.S. Pat. No. 399,216. These systems have the additional advantage of the ability to splice out introns and thus can be used directly to express genomic fragments. These systems can also provide prost-translational modification mimicing those occurring in some natural proteins. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV40) (Fiers, et al., Nature (1978) 273:113), or other viral promoters such as those derived from polyoma, Adenovirus 2, bovine papilloma virus, or avian sarcoma viruses. The controllable promoter, hMT-II$_A$ (Karin, M., et al. Nature (1982) 299:797-802) may also be used. General aspects of mammalian cell host system transformations have been described by Axel (supra). It is apparent that "enhancer" regions are also important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

TRANSFORMATIONS

Depending on the host cell used, transformation is done using standard techniques appropriate to such cells. The calcium treatment employing calcium chloride, as described by Cohen, S. N. PNAS (1972) 69:2110, or the RbCl$_2$ method described in Maniatis, et al., Molecular Cloning: A Laboratory Manual (1982) Cold Spring Harbor Press, p. 254 and Hanahan, D., J. Mol. Biol. (1983) 166:557-580 may be used for procaryotes or other cells which contain substantial cell wall barriers. For mammalian cells without such cell walls, the calcium phosphate precipitation method of Graham and van der Eb, Virology (1978) 52:546, optionally as modified by Wigler, M., et al., Cell (1979) 16:777-785 may be used. Transformations into yeast may be carried out according to the method of Beggs, J. D., Nature (1978) 275:104-109 or of Hinnen, A., et al , PNAS (1978) 75:1929.

VECTOR CONSTRUCTION

Construction of suitable vectors containing the desired coding and regulatory elements for expression of the DNA sequences provided herein employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in the constructions. Typical sequences have been set forth in Hosts and Control Sequences above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See for example, Edge, M. D., Nature (1981) 292:756; Nambair, K. P., et al., Science (1984) 223:1299; Jay, Ernest, J. Biol. Chem. (1984) 259:6311.

Synthetic oligonucleotides are prepared by either the phosphotriester method as described by Edge, et al., Nature (supra) and Duckworth, et al., Nucleic Acids Res. (1981) 9:1691 or the phosphoramidite method as described by Beaucage, S. L., and Caruthers, M. H. *Tet. Letts.* (1981) 22:1859 and Matteucci, M. D., and Caruthers, M. H., *J. Am. Chem. Soc.* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles $\gamma$-$^{32}$P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 $\mu$g of plasmid or DNA sequence is cleaved by one unit of enzyme in about 20 $\mu$l of buffer solution: in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° to 25° C. in 50 mM Tris pH 7.6, 50 mM NaCl, 6 mM $MgCl_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15-50 $\mu$l volumes under the following standard conditions and temperatures: for example, 60 mM Tris-Cl pH 7.5, 16 mM $MgCl_2$, 10 mM DTT, 33 $\mu$g/ml BSA, and either 40 $\mu$M ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 $\mu$g/ml total DNA concentrations (5-100 nM total end concentration). Intermolecular blunt end ligations are performed at 1 $\mu$M total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP per $\mu$g of vector at 60° C. for about one hour, or in 50 mM Tris-HCl (pH 9.0), 1 mM $MgCl_2$, 0.1 mM $ZnCl_2$, 1 mM Spermidine, 1 unit CIP at 37° C. for 60 minutes (for protruding 5' ends) or 15 minutes at 37° C. and then 15 minutes at 56° C. (for blunt ends or recessed 5' ends). In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res.* (1982) 10:6487-6500 and Adelman, J. P., et al., *DNA* (1983) 2:183-193). This is conducted using a primer synthetic oligonucleotide, complementary to a single stranded phage DNA to be mutagenized, except for limited mismatching which represents the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. Plaue lifts of the resulting plaques onto nitrocellulose are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

VERIFICATION OF CONSTRUCTION

In the constructions set forth below, correct ligations for plasmid construction are confirmed by first transforming *E. coli* strain MC1061 obtained from Dr. M. Casadaban (Casadaban, M., et al., *J. Mol. Biol.* (1980) 138:179-207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al., *PNAS* (1969) 62:1159, optionally following chloramphenicol amplification (Clewell, D. B. *J. Bacteriol.* (1972) 110:667). Several mini DNA preps are commonly used, e.g., Holmes, D. S. et al., *Anal. Biochem.* (1981) 114:193-197 and Birnboim, H. C., et al., *Nucleic Acids Res.* (1979) 7:1513-1523. The isolated DNA is analyzed by restriction and/or sequenced by the dideoxy nucleotide method of Sanger, F. et al., *PNAS* (1977) 74:5463 as further described by Messing, et al., *Nucleic Acids Res.* (1981) 9:309, or by the method of Maxam, et al., *Methods in Enzymology* (1980) 65:499.

HOSTS EXEMPLIFIED

Host strains used in cloning and prokaryotic expression herein are as follows:

For cloning and sequencing, and for expression of constructions under the control of most bacterial promoters, *E. coli* strains such as B, MC1061, DH1, RRI, C600hfl−, K803, HB101, JA221, JM101, and JM103 were used.

ILLUSTRATIVE PROCEDURES

The following examples are intended to illustrate the invention as a means of better understanding it. The examples are not, however, intended to limit the scope of the invention in any way. The DNA encoding vascular endothelial cell growth factor is obtained initially by first obtaining a pivotal probe by means of amplification of the desired sequence in a preparation of folliculo stellate poly(A)+ RNA. However, it would not be necessary to repeat the procedure, since the sequence of the pivotal probe is now known and could thus be constructed chemically in vitro. In addition, a plasmid containing the sequence illustrated in FIG. 3a as been deposited at the American Types Culture Collection, Rockville, Md.

In the following examples the buffers described below have the indicated compositions:

| Buffer | Composition |
|---|---|
| 40% Formamide | 50 mM HEPES pH 7.0 |
| | 40% formamide |
| | 5 × Denhardt's (50x = 1% Ficoll; |
| | 1% polyvinylpyrollidone; |
| | 1% bovine serum albumin) |
| | 5 × SSC (20 × SSC = 3M NaCl; |
| | 0.3M sodium citrate) |
| | 50 μg/ml sheared DNA |
| 50% Formamide | Same as above, but substitute 50% formamide for 40% formamide |
| Short Oligo Prehybridization | Same as above, but with no formadide added |
| Long Oligo Prehybridization | 6 × SSC |
| | 50 mM sodium phosphate (pH 6.8) |
| | 5 × Denhardt's |
| | 100 μg/ml sheared DNA |
| | 20% formamide |

EXAMPLE 1

Amplification of Probe from Folliculo Stellate Cell mRNA

Referring to FIG. 2, 5 μg of poly(A)+ RNA from bovine folliculo stellate cells (cells are isolated as described in Ferrara, N. et al., (1986) In: *Methods in Enzymology*, Conn, P. M. ed., Vol. 124, pp 245-253, Academic Press, N.Y.; Ferrara, N. et al., (1987) *PNAS*, 84:5773-5777) was ethanol precipitated with 1 μg of an anti-sense priming oligonucleotide based on the known amino acid sequence of amino acids no. 35 to 39 of bovine vascular endothelial cell growth factor. The oligonucleotide, designated #4296, was a 24-mer having a 16-fold degeneracy. The degeneracy was confined to a region of 14 bases corresponding to the antisense sense strand of the coding region for amino acids 35 to 39. At the 5' end of the 14 bases there was added a 10-base linker containing an EcoRI restriction site. The sequence of the oligonucleotide primer was as follows:

The mRNA and oligonucleotide were dissolved in 55 μl of 36 mM KCl, 9 mM MgCl₂, 45 mM Tris pH 7.5, 12 units RNasin and 0.5 mM each of the four dNTPs. The sample was heated to 70° C. for 2 minutes and then was brought to room temperature. For synthesis of a DNA anti-sense strand complementary to a portion of the mRNA adjacent to the site of hybridization of the primer, 60 units of avian myeloblastosis virus reverse transcriptase was added, and the reaction was allowed to stay at room temperature for 2 minutes and then brought to 42° C. for 45 minutes. The sample was then extracted with phenol and chloroform, precipitated with ethanol and dried.

A second DNA strand was then synthesized using all of the first synthesized strand as template. For second strand synthesis, the dried pellet was dissolved in 50 μl of 50 mM NaCl, 7 mM MgCl₂, 7 mM Tris pH 7.5 and 1 mM each of the four dNTPs. There was also added 1 μg sense strand oligonucleotide primer, which was based on the known amino acid sequence of bovine vascular endothelial cell growth factor at amino acid positions no. 15 to 19. The oligonucleotide, designated #4295, was a 24-mer with an 8-fold degeneracy. The degeneracy was confined to the 14-base region corresponding to the sense strand of the coding region for amino acids 15 to 19. At the 5' end of these 14 bases there was added a 10-base linker containing a HindIII restriction site. The sequence of the oligonucleotide primer was as follows:

The sample was heated to 100° C. for 2 minutes and then brought to 28° C. Second strand synthesis was carried out at 28° C. for 10 minutes with the addition of 10 units of DNA polymerase I, Klenow fragment. Afterwards, the polymerase enzyme was inactivated by heating at 100° C. for 2 minutes.

The DNA sequence extending between the two primer hybridization sites was amplified by a repetitive series of enzymatically catalyzed polymerization reactions using an automated thermal cycler (Perkin Elmer Cetus DNA Thermal Cycler). For the chain reaction 5 μl of the above reaction was brought to 100 μl in 1×reaction mix by the addition of 10 μl 10X Taq buffer mix (supplied in a polymerase chain reaction kit from Cetus Corp.), 52 μl dH₂O, and 16 μl containing all 4 dNTPs at 1.25 mM each. In addition, 10% DMSO (final concentration) and 1 μg of each of the sense and anti-sense oligonucleotides described above were added, along with 2 μl of Taq polymerase supplied in the Cetus kit. The reaction mix was covered with 200 μl of mineral oil and placed in the thermal cycler. The cycler was programmed to repeat the following cycle:

1. Denature at 94° C., 1 minute
2. Anneal at 55° C., 2 minutes
3. DNA synthesis at 72° C., 3.5 minutes The amplification reaction was carried out for 30 cycles.

A portion of the DNA from the amplification reaction (20 μl) was loaded onto a 6% polyacrylamide gel and subjected to electrophoresis using HaeIII-digested pUC8 DNA to provide size markers. The gel was stained with ethidium bromide. The stained gel is shown in FIG. 5. A major band (marked with an arrow in FIG. 5) running between 80 and 100 base pairs corresponded to the appropriate length DNA (94 base pairs) to encode the two oligonucleotide primers as well as the amino acid coding region segment bracketed by the two primers. This band was cut from the gel and the DNA was electroeluted from the gel slice at 30 volts in 0.5×Tris borate EDTA buffer (0.045 M Tris base, 0.045 M boric acid, 0.001 M EDTA). The DNA obtained was precipitated with ethanol.

EXAMPLE 2

Subcloning and Sequencing of Amplified Probe

The DNA that was electroeluted from the gel as described in Example 1 was subcloned in bacteriophage M13mp18 and M13mp19. One-half of the DNA obtained from the gel was dissolved in 20 μl of water and digested with HindIII in strandard HindIII digestion buffer for 90 minutes at 37° C. The concentration of Tris-HCl (pH 7.5) in the reaction was raised to 85 mM, EcoRI was added and the reaction was incubated a further 90 minutes at 37° C. In separate reactions, approximately one-tenth of the digested preparation per reaction was then ligated, in the presence of T4 DNA ligase, with M13mp18 phage and M13mp19 phage double-stranded DNA (Yanisch-Perron, et al., *Gene* (1985) 33:103) that had been cut with HindIII and EcoRI. Each ligation mix was then transfected into *E. coli* JM103 using standard techniques and plated onto L plates containing 5-bromo-4-chloro-3-indolyl-β-D-galactopyranoside (X-gal) and isopropyl-β-D-thiogalactopyranoside (IPTG). In the case of the M13mp19 reaction, after plaques formed on the plates, portions of the plaques were lifted onto nitrocellulose filter paper, lysed by treatment with NaOH according to standard techniques, and baked for 2 hours at 80° C. in a vacuum oven. In order to screen for the presence of the desired insert sequence, the plaque lift was probed with a radiolabelled sample of the oligonucleotide primer #4296. Probe #4296 hybridized to numerous plaques on the plaque lift and four were chosen for further analysis. In the case of the M13mp18 reaction, four plaques for further analysis were picked based on the fact that they were white, indicating that an insert fragment had been ligated between the EcoRI and HindIII sites of the phage vector.

The four plaques from each of the M13mp18 and M13mp19 infected plates that were picked were used to infect JM103 and replicative form (RF) DNA was prepared from the infected cultures using standard techniques. The RF DNA from each infection was then cut with HaeIII and loaded onto a polyacrylamide gel. Electrophoresis was conducted using HaeIII-cut pUC8 and HaeIII-cut M13mp18 RF as size markers. Upon visualization with ethidium bromide, the DNA in all eight sample lanes was shown to contain an insert of the correct size to encode the amino acid sequence lying in the region between and including the amino acids used to design the primers used in the polymerase chain reaction.

One of the M13mp19 plaques and the four M13mp18 plaques shown to have the correct insert sequence length were picked for further analysis. Single stranded DNA was then prepared for sequencing according to standard procedures (see Messing, J., *Methods in Enzymology* (1983) 101:20–78). The sequences of the inserts in the five isolated clones are given in FIG. 1. One region of the sequencing gel (nucleotides 32-35 in FIG. 1) was not unambiguously readable for the four M13mp18 clones. Excluding the unreadable region of the M13mp18 sequences, four of the five sequenced clones encoded the same amino acid sequence corresponding to that portion of the bovine vascular endothelial cell growth factor encoded by the mRNA region extending between and including the hybridization sites of the two primer sequences used in the polymerase chain reaction. The fifth sequenced clone contained a single encoded amino acid difference, encoding His (CAC), rather than Pro (CCC), at the position corresponding to amino acid no. 27 of bovine vascular endothelial cell growth factor. FIG. 1 gives the DNA sequences of the inserts in the five clones, as well as a consensus DNA sequence and the deduced amino acid sequence for the insert in the M13mp19 clone. It can be seen that most of the non-homologous nucleotides between the five isolated sequences occurred at positions located in the primer sequences used in the polymerase chain reaction, indicating that in some instances degenerate oligonucleotides in the primers having single-nucleotide mismatches may have hybridized with the protein-encoding sequence in the vascular endothelial cell mRNA and subsequently been amplified. Other sequence differences presumably were the result of either polymerase errors or polymorphisms in the vascular endothelial cell growth factor mRNA. While these sequences may not correspond precisely to the native DNA sequence, four of the five nonetheless encode the correct amino acid sequence (excluding the unreadable region in the M13mp18 clones) for vascular endothelial cell growth factor. Moreover, they can be used as probes to isolate full-length DNA sequences for bovine vascular endothelial cell growth factor or for isolating DNAs encoding the corresponding protein in non-bovine species. The picked phage in which the amplified DNA had been ligated into M13mp19 was renamed pET-19A; the inserted fragment in this phage was used as the probe to screen a folliculo stellate cell cDNA library, as described in Example 3 below.

EXAMPLE 3

Retrieval of cDNA Encoding Bovine Vascular Endothelial Cell Growth Factor (120-Amino Acid Form)

A bovine folliculo stellate cell cDNA library was prepared in λgt10 bacteriophage according to a modification of the procedure of Huynh, et al., in DNA Cloning, D. M. Glover ed., Vol. I, p. 49, IRL Press, Washington, D.C. (1985). The poly(A)+ RNA used to make the cDNA for the library was obtained from folliculo stellate cells isolated and expanded from bovine pituitary by Dr. Denis Gospodarowicz according to published procedures (Ferrara, et al., *PNAS* (1987) 84:5773-5777). The cDNA library (approximately 1.5×10⁶ phage) in λgt10 was plated on C600hfl− cells (30 plates, 5×10⁴ phage/plate). Two plaque lifts from each plate were made onto nitrocellulose filter papers. The filters were immersed in a denaturing solution (0.2 M NaOH, 1.5 M NaCl) for 3 minutes, followed by a neutralization solution (2 × SSC, 0.4 M Tris pH 7.5) for 3 minutes and a wash solution (2 × SSC) for 3 minutes. The filters were then air-dried and baked at 80° C for 2 hours in a vacuum oven. One set of the filters was prehybridized in 200 ml of 40% Formamide Buffer at 42° C.

To prepare a probe for screening the filters a single-stranded preparation was made of the M13mp19-derived phage pET-19A, isolated as described in Example 2 above, using standard methods (Messing, J., *Methods Enzymol.* (1983) 101:20–78). This preparation was annealed with the "universal" primer (Messing, J., *Methods Enzymol.* (1983) 101:20–78), and a complementary strand for pET-19A was synthesized by extending the primer using Klenow-fragment polymerase and $\alpha^{32}$P-dNTPs.

One set of plaque lifts was screened with this radiolabelled probe. The probe was heated to 100° C. for 2 minutes to melt the double-stranded DNA and then set on ice. The probe (1 ml; $5 \times 10^8$ cpm) was then added to the 200 ml of 40% Formamide Buffer used for prehybridization and mixed thoroughly. The prehybridized filters were added and incubated overnight at 42° C. in a rocking water bath. The filters were then washed in 1 × SSC(20 × SSC equals 3M NaCl, 0.3M Na citrate) containing 0.1% SDS for several hours at 50° C. After washing, the filters were exposed to X-ray film at −70 to −80° C. overnight.

Approximately 32 putative positive clones were identified in the initial screen with the primer-extended probe derived from pET-19A. Ten clones, identified 1c-10c were selected for further screening.

The second set of plaque lifts was screened with a radiolabelled synthetic oligonucleotide probe designed on the basis of the sequence obtained for the amplified DNA insert in pET-19A, shown in FIG. 1. The oligonucleotide, identified as probe #4340, was a 39-mer oligonucleotide corresponding to the anti-sense strand and having the nucleotide sequence:

5'-CAC CAG GGT CTC GAT GGG ACG GCA
GAA GCT GCG CTG GTA-3'

The filters were pre-hybridized in 100 ml of Long Oligo Prehybridization Buffer at 43° C for approximately 6 hours. The filters in the pre-hybridization buffer were then heated for 10 minutes in a 65° C. water bath. The probe ($5 \times 10^8$ cpm), radiolabelled using $\gamma$-$^{32}$P-ATP and polynucleotide kinase, was added to the 65° C. buffer and the temperature was slowly cooled to room temperature by shutting off the heat to the water bath. The following day, the filters were removed from the hybridization buffer and washed for 2 hours [6~in 3 × SSC, 0.1% SDS at 45° C. with a change of wash buffer at 1 hr. The filters were dried and exposed to X-ray film overnight at −70 to −80° C.

Of the clones that hybridized with probe #4340, only one clone appeared to correspond to one of the 32 clones from the first set of filters that had hybridized with pET-19A. This clone was not one of the original 10 picked for further analysis; therefore, the clone was picked and designated clone 11c. The filters probed with #4340 were rewashed under more stringent conditions (1 × SSC, 0.1% SDS, 65° C.), whereupon the number of putative positive clones was reduced to approximately 6, including the clone 11c which had hybridized with pET-19A.

The picked clones 2c-11c were plated out for a second round of screening. To "pick" the clones, plugs of each clone were removed from the appropriate areas of the agar plates by placing the open end of a sterile Falcon 12×5 mm 75 mm tube over the desired area of the plate corresponding to the positive signal on the filter lifted from the plate, pushing the tube down through the agar, and picking up the plug with a sterile spatula. Each plug was then placed into 1 ml SM buffer (100 mM NaCl; 8 mM MgSO$_4$; 50 mM Tris pH 7.5; 0.01% gelatin), vortexed, and allowed to sit approximately 20 minutes at room temperature to allow the phage to diffuse out of the agar. One $\mu$l of the resulting suspension for each picked clone was suspended in 1 ml of SM buffer (1:1000 dilution). 10 $\mu$l of each 1:1000 phage dilution was then transferred to a Falcon 75×100 mm tube containing 590–600 $\mu$l of plating cells (C600hfl−) and then serially diluted out by transferring 10 $\mu$l from this tube to a second tube containing 590–600 $\mu$l of plating cells, and from that tube to a third tube. Phage were absorbed for 20 minutes at 37° C. and the phage/C600hfl− mix in each tube was plated out with approximately 10 ml of top agarose in 150 mm agar plates. The plates were incubated overnight at 37° C. Plates having approximately 5,000 phage per plate were used to make plaque lifts onto nitrocellulose filter papers. The DNA on the filters was then denatured by treating the filters with NaOH in the same manner described above for the plaque lifts from the primary screen of the cDNA library. After baking, the filters were prehybridized by immersing them in plastic sealable bags (3 filters/bag) each containing 10 ml of 50% Formamide Buffer, in a rocking water bath for 2 hours at 42° C.

To prepare a probe for screening the filters a double-stranded (replicative form) preparation was made of the M13mp19-derived phage pET-19A. This preparation was digested with EcoRI and HindIII and the 82-base pair insert fragment representing the amplified DNA segment was isolated by gel elctrophoresis and then labelled by filling in single-stranded ends with Klenow-fragment polymerase and $\alpha^{32}$P-dNTPs. The probe was boiled for 2 minutes to melt the double-stranded DNA, cooled on ice and then added to the prehybridization buffer in which the filters were immersed. The filters were incubated overnight in a rocking water bath at 42° C. and washed in 0.1 × SSC, 0.1% SDS wash buffer at 50° C. for 1½ hours with two buffer changes. The filters were exposed to X-ray film overnight at −70° to −80° C.

Three positive clones on the plate representing the re-plating of clone 11c hybridized to the 82 base pair insert fragment from pET−19A. In addition, there appeared to be one questionable positive clone on the plate representing the re-plating of clone 7c. These four positive clones were excised from the agar plates using the wide end of a Pasteur pipet, diluted in plating cells and re-plated for a third round of screening in a manner similar to that previously described. The three plates produced for the third round screening of the three positive clones on the plate representing clone 11c in the second round screening were designated 11A, 11B and 11C. Two plaque lifts were prepared from each plate on nitrocellulose filter paper, as previously described. The DNA on the filters was denatured and baked using procedures similar to those described above. The first set of plaque lifts was screened with radiolabelled probe #4340 (previously described) and the second set of plaque lifts was screened with the previously described probe prepared from the 82 base pair insert of pET−−19A.

The first set of filters was prehybridized by immersion in plastic bags containing 7 ml of Short Oligo Prehybridization Buffer at room temperature. Radiolabelled probe #4340 was added to the prehybridization buffer containing these filters. The temperature was brought to 65° C. by placing the bags for a few minutes in a shaking water bath set at 65° C. The heat for the water bath was then shut off, allowing the temperature to return slowly to room temperature. Incubation was allowed to proceed for approximately 2½ days at room temperature.

The second set of filters was prehybridized by immersion in plastic bags containing 10 ml of 50% Formamide Buffer, and incubation at 42° C. The probe prepared from the 82 base pair insert of pET-19A was boiled and added directly to the prehybridization buffer containing the second set of filters. The hybridization reaction was incubated at 42° C. in a rocking water bath for approximately 2½ days.

The set of filters hybridized with probe #4340 was washed in 1 × SSC, 0.1% SDS at 55° C. The set of filters hybridized with the probe derived from pET-19A were washed at 55° C. in 0.1 × SSC, 0.1% SDS. Both sets of filters were exposed to X-ray film for 3½ hours. Several plaques on plates 11A, 11B and 11C hybridized strongly to both probe #4340 and the 82 base pair insert from pET-19A. No plaques on the plate representing a dilution of the pick from plate 7c of the second round screening hybridized to either probe. Two strongly hybridizing plaques from plate 11A were picked using the thin end of a Pasteur pipet. These clones, designated 11A' and 11B', were diluted in plating cells and replated, as previously described, for a fourth round of screening.

Two plaque lifts were prepared on nitrocellulose filter paper from each of the plates prepared from positive clones 11A' and 11B'. The DNA on the filters was denatured and baked using procedures similar to those described above. Each set of filters was prehybridized by immersion in a plastic bag containing 10 ml of Short Oligo Prehybridization Buffer and incubating at room temperature. The first plaque lift from each of plates 11A' and 11B' was screened with radiolabelled probe #4340 (previously described). The probe was added to the plastic bag containing the filters and prehybridization buffer and incubated first at 65° C. and then with slow cooling as described above. The second plaque lift from each of plates 11A' and 11B' was screened with a radiolabelled 48-fold degenerate mixed oligonucleotide probe, identified as probe #4255, which was based on the amino acid sequence derived from an internal tryptic fragment of bovine vascular endothelial cell growth factor and which has the sequence

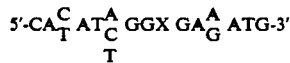

The hybridization conditions were the same as just described for probe #4340. The plaque lifts from plates 11A' and 11B' were washed with 1 × SSC, 0.1% SDS at 55° C. (#4340) or 3 × SSC, 0.1% SDS at 30° C. and then with 3M tetramethylammonium chloride (TMACl), 0.05M Tris-HCl, pH 8.0, 0.1% SDS, 0.002M EDTA at 45° C. (#4255) and exposed to film. The plaques from both plates were found to hybridize to both probe #4340 and probe #4255, with all plaques on each filter hybridizing. It was concluded that clones 11A' and 11B' constitute single, pure clones.

The DNA insert in clone 11B' was sequenced by first digesting the phage DNA with EcoRI, fractionating the digest on a 6% polyacrylamide gel, electroeluting the approximately 800 base pair insert fragment, and ligating the fragment into EcoRI-cut M13mp18. The insert was then sequenced by the dideoxynucleotide procedure, using standard methods. The nucleotide sequence, as well as the encoded amino acid sequence, is shown in FIG. 3a (only nucleotides 7 through 795 of the 797-nucleotide insert sequence are shown in the figure; the EcoRI linker sequences on each end have been omitted). The 797-nucleotide insert sequence encodes the known portion of the amino acid sequence of bovine vascular endothelial cell growth factor, beginning at amino acid no. 15 of the known protein sequence. The open reading frame extends to an in-frame translation stop codon at nucleotide 327. The insert sequence of clone 11B' was ligated into the EcoRI site of plasmid pUC8. The resulting plasmid, designated pST800, has been deposited in an E. coli JM83 host at the American Type Culture Collection, Rockville, Md. with Accession No. 68060.

A full length coding sequence for a mature form of bovine vascular endothelial cell growth factor is represented by the sequence of FIG. 3a, taken together with the sequence in FIG. 3b. The double stranded DNA sequence shown in FIG. 3b, with the translation initiation codon, ATG, near its 5' end, represents a sequence of nucleotides, selected on the basis of preferred codon choice for gene expression in human cells, which encodes the indicated N-terminal portion of the bovine protein (preceded by an initiating methionine residue) and which overlaps the coding sequence shown in FIG. 3a. The DNA sequence of FIG. 3b can be synthesized using known methods of oligonucleotide synthesis and enzymatically joined to a portion of the sequence shown in FIG. 3a, which can be conveniently obtained from the plasmid deposited at ATCC, in order to produce a full-length coding sequence for a mature form of bovine vascular endothelial cell growth factor. Before the sequences in FIGS. 3a and 3b are joined, the sequence in FIG. 3a is excised from the plasmid pST800 using EcoRI, and the isolated insert is digested with NlaIV which cuts the insert five times, all within the 3' untranslated region. A linker encoding a convenient restriction site, e.g. HindIII, is then joined at the 5'-most NlaIV site via blunt-end ligation. The resulting ligation mix is then digested with AccI and the linker enzyme (e.g. HindIII), to release a 325 base pair fragment (AccI-NlaIV) of the pST800 insert with a digested linker ligated at the 3' end (at the NlaIV site). This fragment is purified and ligated to the synthetic fragment shown in FIG. 3b. After digestion of the ligation mix with NcoI and the restriction enzyme that cleaves the linker (e.g. HindIII, if a HindIII linker is used), a fragment is produced with the desired coding sequence for a mature form of bovine vascular endothelial cell growth factor, flanked on the 5' side with a digested NcoI site, and on the 3' side by a digested restriction site useful for insertion of the fragment into an expression vector.

The composite sequence is inserted into an appropriate expression vector under the control of regulatory elements capable of directing its expression in a prokaryotic or eukaryotic host. For expression in E. coli, a convenient vector would be pKK233-2 (Amman and Brosius, Gene (1985) 40:183–190), which is commercially available from Pharmacia, Inc. Insertion of the composite sequence between the NcoI and HindIII sites of this vector would place the coding sequence under the control of the trc promoter. The expression vector is then used to transform a suitable host, such as E. coli and the transformants are cultured under conditions in which the encoded DNA is expressed. The expressed protein is then recovered by means which are conventional in the art.

Of course, other sequences could be joined to the sequence in FIG. 3a. For example, the sequence in FIG. 3b could be altered so that the 5' end represents an NdeI site, rather than NcoI. For expression in mammalian cells the coding sequence in FIG. 3b could be extended in the 5' direction such that it encodes the amino-terminal sequence of bovine vascular endothelial cell growth factor operably joined to a secretion signal sequence, e.g. the signal sequence for human growth hormone.

Alternatively, the coding sequence represented by FIG. 3a can be used as a probe, under standard conditions for DNA hybridization, to retrieve native, full-length DNA sequences encoding bovine vascular endothelial cell growth factor or the corresponding protein in other mammalian species, including man. The sequence of FIG. 3a can be used as a probe to retrieve the desired sequences from either cDNA or genomic DNA libraries.

Clones extended toward the 5' end of the bovine vascular endothelial cell growth factor mRNA were generated by priming first-strand cDNA synthesis as described above in Example 1 using as a primer the antisense oligonucleotide 4338 (5'-GCCAAGCTT-GCACCAGGGTCTCGATGGGACG-GCAGAA—3') and then ligating onto the 5' end of the resulting duplex a partially double-stranded linker molecule consisting of the oligonucleotides no. 4537 and 4514 (5'-GATCGCGG—3' and 5'-CCGCGAT-CAAGCTTCCCGGGAATTCGGC—3', respectively). Finally, the products were amplified by polymerase chain reaction using as primers the oligonucleotides 4338 and 4315 (5'-GCCGAATTCCCG-GGAAGCTTGATCGCGG; complementary to 4514). Upon sequencing by the dideoxynucleotide method, the resulting clones gave the 5' sequences shown in FIG. 6.

EXAMPLE 4

Retrieval of cDNA Encoding Bovine Vascular Endothelial Cell Growth Factor (bVEGF$_{164}$)

To isolate VEGF forms other than bVEGF120 (FIG. 3a), first-strand cDNA synthesis was carried out using folliculo stellate poly(A)+RNA as a template and using as a primer the antisense oligonucleotide 4456 (5'-GTAGTTCTGTGTCAGTCTTTCCTGGT-GAGACGTCTGGTTCCCGAAACCCTGAGG-GAGGCT —3'). The resulting products were then amplified by 30 rounds of polymerase chain reaction, using as primers the antisense oligonucleotide 4456 and the sense oligonucleotide 4414 (5'-TTCTGCCGTCCCATCGAGACCCTGGT-GGACATCTTCCAGGAGTACCCAGAT-GAGATT-3'). Polyacrylamide gel analysis and DNA sequencing of the products revealed two species of cDNA encoding vascular endothelial cell growth factor, as shown in FIG. 6. The open reading frame which includes the 132 bp insert shown in the box in FIG. 6 encodes bVEGF$_{164}$.

EXAMPLE 5

Retrieval of Genomic DNA Encoding Human Vascular Endothelial Cell Growth Factor

Human genomic clones containing DNA encoding amino acid sequences of vascular endothelial cell growth factor were isolated from a commercially available human lung fibroblast genomic library (Stratagene Inc., La Jolla, Calif.). One μl of stock phage (approximately 3×10$^{10}$ phage/ml) was diluted into 1 ml SM Buffer and 20 μl of CHCl$_3$ were added. LE 392 cells (hsdR514 (r−,m−), supE44, supF58, lacY1 or Δ(lacI-ZY)6, galK2, galT22, metB1, trpR55, λ−) were grown in NZYM medium to an O.D.$_{600}$ of 0.5 and the cells were spun out and resuspended in 10 mM MgSO$_4$. In each of 30 tubes, 2 μl of diluted phage stock were mixed with 0.6 ml of cells and incubated at 37° C. for 15 minutes. Ten ml of NZYM top agar were added to each tube, and the contents of each tube were plated out on a 150 mm NZYM plate and incubated at 37° C. for 16 hours before reducing the temperature to 4° C. Two plaque lifts onto nitrocellulose filter paper were taken from each of the 30 plates. The DNA on the filters was denatured and baked as described above in Example 3. The filters were then prehybridized in 40% Formamide Buffer at 37° C. for 6 hours.

The filters were probed with a radiolabelled probe which had been prepared by nick translation of gel-purified EcoRI insert fragment from the plasmid pST800, a plasmid made as described in Example 3 above. The 797 base pair EcoRI insert of pST800 contains a cDNA fragment encoding a portion of bovine vascular endothelial cell growth factor. The probe was boiled at 100° C. for 2 minutes to melt the double-stranded DNA and then cooled on ice. The probe was added directly to the prehybridization buffer containing the filters at 10$^6$ cpm/ml and the filters were hybridized overnight at 37° C. The filters were washed in 1 × SSC, 0.1% SDS at 50° C. with 3 changes of wash buffer, then blotted dry and exposed to X-ray film overnight at −70° to −80° C. The exposed films indicated approximately 200 positives per plate with 19 clones being characterized as strong positives.

Of the 19 strong positives, 12 were picked and diluted as described in Example 3 above, and replated for a second round of screening. Two sets of plaque lifts were prepared, as previously described, from the replated phage. The filters were prehybridized in 40% Formamide suffer at 37° C. for 6 hours. One set of filters was hybridized overnight at 37° C. with the same probe used in the first round screen. The other set of filters was hybridized with nick-translated radiolabelled pUC8 in order to ensure that the picked positives from the first round were not hybridizing with sequences derived from the vector used to subclone the probe sequence. The filters were washed in 1 × SSC, 0.1% SDS at 50° C., and exposed to film. On this second round screening, six out of the twelve replated clones were still positive with the probe derived from pST800, and not with the pUC8 probe.

Positive plaques were picked representing each of the six positive clones in the second round screen. The six picked plaques were diluted as before and replated for a third round of screening. Additionally, the 7 strong positive clones from the first round which had not been rescreened were also picked and replated for a second round of screening. Two plaque lifts were prepared, as previously described, from each of the replated clones. The filters were prehybridized in 40% Formamide Buffer at 37° C. for 5 hours.

To one set of plaque lifts of the 6 positive clones from the second round of screening there were added 10$^6$ cpm/ml of the nick-translated 797-base pair insert probe derived from pST800 as previously described. The filters and probe were hybridized overnight at 37° C. in the prehybridization buffer. To the second set of plaque lifts of these 6 positive clones there was added a probe which was prepared by nick-translation of an EcoRI- HpaII fragment of the aforementioned 797-base pair insert of pST800. The EcoRI-HpaII fragment consisted of 331 base pairs at the 5' end of the 797-base pair insert, thereby eliminating the 3' end of the insert which was rich in A and T nucleotides and may have accounted for false positive hybridizations in earlier screening rounds. The probe was hybridized in the prehybridization buffer overnight at 37° C.

To both sets of plaque lifts of the 7 replated first round positive clones there were added $10^6$ cpm/ml of the nick-translated 797-base pair probe. The probe was hybridized in the prehybridization buffer overnight at 37° C.

All of the filters were washed in 1 × SSC, 0.1% SDS at 50° C. for 2 hours with 2 changes of buffer. The filters were dried and exposed to X-ray film at −70° to −80° C. for 3 hours. Of the 7 first round positive clones, 4 gave positive signals with the 797-base pair probe, on the second-round screening. Of the 6 positive clones from the second round screening, 4 gave positive signals with both the 797-base pair and 331-base pair probes on the third round screening.

The 4 second-round positives were picked and subjected to a third round of screening, with one set of plaque lifts being screened with the radiolabeled 797-base pair probe, and the other set being hybridized with the radiolabeled 331-base pair probe, as described above. All 4 were found to hybridize with both probes.

All eight clones that hybridized on the third round screening with both the 797-base pair and 331-base pair probes were picked as single plaques. Phage DNA preps were prepared according to standard methods. Fragments of the genomic DNA inserts in the phage were then transferred to M13mp18 and M13mp19 phage for sequencing, to confirm that they encoded human vascular endothelial cell growth factor. One of the bacteriophage containing a genomic clone encoding human vascular endothelial cell growth factor has been deposited at the American Type Culture Collection, with accession number ATCC 40636.

EXAMPLE 6

Retrieval of cDNA Encoding Human Vascular Endothelial Cell Growth Factor

Cell Source of Vascular Endothelial Cell Growth Factor mRNA

Vascular smooth muscle cells produce high levels of mRNA encoding the vascular endothelial cell growth factor protein and are therefore a good source of mRNA for the preparation of a cDNA library enriched in vascular endothelial cell growth factor sequences. Fetal human vascular smooth muscle (fhVSM) cells are cultured in low glucose Dulbecco's Modified Eagle's Medium (DMEM-16, GIBCO) supplemented with 10% (v/v) Fetal Bovine Serum (HYCLONE), 2 mM L-glutamine, 100 U each of penicillin and streptomycin per ml, and recombinant human basic fibroblast growth factor (added at a concentration of 1 ng/ml every 48 hours). Cells are subcultivated at confluence, and are typically seeded at 25% confluence.

Poly(A)+ RNA Isolation

For the isolation of vascular smooth muscle cell mRNA, the cells are typically grown to confluence and then treated or not with phorbol myristate acetate (PMA) to additionally stimulate synthesis of vascular endothelial cell growth factor mRNA. The cell monolayer is rinsed twice with 5 to 20 ml of Dulbecco's Phosphate Buffered Saline (D-PBS) to remove residual media before isolating RNA according to the methods of Chirgwin et al., *Biochemistry* (1979) 18:5294–5299. With this method, cells in the monolayer are lysed by the direct addition of a lysis buffer (4.0M guanidine thiocyanate, 0.1% Antifoam A, 25 mM sodium citrate, 0.5% N-lauroyl sarcosine, and 100 mM β-mercaptoethanol). After shearing DNA by passage through a syringe needle, RNA is directly precipitated by the addition of acetic acid and ethanol. The precipitated RNA is then resuspended in diethylpyrocarbonate (DEP)-treated deionized water (D-H$_2$O, typically about 400 μl) and 2.6 ml of guanidine-HCl buffer (7.5M guanidine hydrochloride, 25 mM sodium citrate, 5 mM dithiothreitol) is added and the RNA precipitated by the addition of acetic acid and ethanol. The precipitated RNA is again resuspended in about 400 μl of DEP-treated d-H$_2$O and precipitated by the addition of sodium acetate and ethanol.

Total cellular RNA isolated by the guanidinethiocyanate procedure (above) is further fractionated by oligo d(T)-cellulose chromatography to isolate poly(A)+ RNA following established procedures (Edmonds, M., et al., *PNAS* (1971) 68:1336; Aviv, H. and Leder, P., *PNAS* (1972) 69:1408).

cDNA Synthesis and Cloning of Vascular Endothelial Cell Growth Factor cDNA in λZAPII cDNA synthesis is performed according to the methods of Gubler and Hoffmann (*Gene*, 25:263–269) using a cDNA synthesis kit purchased from Boehringer-Mannheim Biochemicals. The method is briefly described as follows: first strand cDNA synthesis is primed using oligo d(T)$_{15}$ as a primer to begin synthesis by reverse transcriptase from the 3'-ends in 5–20 μg of fhVSM poly (A)+ RNA. Limited digestion of the resulting RNA-DNA hybrid with RNase H provides 3'-OH primers for synthesis of the second DNA strand using *E. coli* DNA polymerase I. T$_4$ DNA polymerase is then used to remove any remaining overhanging 3'-ends, yielding a blunt-ended cDNA product.

Before insertion into a lambda cloning vector such as λZAPII (Stratagene Inc., La Jolla, Calif.), the blunt-ended cDNA is methylated (e.g. with EcoRI methylase) according to standard procedures to block cleavage of a particular subset of the restriction sites present in the cDNA (i.e., methylation with EcoRI methylase will block cleavage of the cDNA by EcoRI). The cDNA is then ligated to oligonucleotide linkers (e.g. EcoRI linkers, GGAATTCC), the linkers are cleaved with the appropriate restriction endonuclease (e.g. EcoRI), and the cDNA is finally ligated into a suitable cloning site in the lambda vector (e.g. the EcoRI site of λZAPII) after removal of excess linkers. Subsequent to ligating the cDNA to vector arms, the cloned cDNA is "packaged" with a lambda packaging extract such as Gigapack II Gold (Stratagene, Inc., La Jolla, Calif.).

After packaging, the lambda phage are titered on the appropriate host strain (e.g. XL1-Blue, Stratagene, Inc., La Jolla, Calif., for the λZAPII vector), then plated on 150 mm plates of NZYM agar at a titer of between 10,000 and 50,000 pfu/plate. Following growth for 6–8 hours at 37° C., the plates are chilled to 4° C. and plaque lifts onto nitrocellulose (BA85, SCHLEICHER AND SCHUELL) or Hybond-N (AMERSHAM) membranes are prepared according to standard procedures (Benton, W. D. and Davis, R. W., *Science* (1977)

196:180). Clones containing sequences homologous or partially homologous to vascular endothelial cell growth factor sequences are detected by hybridization to $^{32}$P-labeled bovine vascular endothelial cell growth factor probes derived from the cDNA insert in pST800 (Example 3 above) or vascular endothelial cell growth factor sequence-specific oligonucleotides based on the sequence given in FIG. 3a. The hybridizations are carried out in standard hybridization buffers containing between 20% and 50% formamide and between 0 and 10% dextran sulfate, and are performed at between 37° and 42° C. Clones hybridizing to the vascular endothelial cell growth factor probes are subsequently single-plaque purified and the related sequences subcloned into bacteriophage M13 vectors such as M13mp18 and M13mp19 for DNA sequence analysis.

The human cDNA sequence for vascular endothelial cell growth factor can be used to predict the specific amino acid sequence of the human vascular endothelial cell growth factor gene products. The cDNA can also be joined to transcriptional control elements in constructs designed to express the human vascular endothelial cell growth factor protein product in bacteria such as $E.\ coli$, or in yeast or mammalian cells.

EXAMPLE 7

DNA and Amino Acid Sequences of Human Vascular Endothelial Cell Growth Factor (hVEGF121 and hVEGF165)

Following the procedures set forth in Example 6, cDNA clones encoding human vascular endothelial cell growth factor were prepared and isolated. Sequence analysis of several clones confirmed that alternative message splicing occurs analogously to the bovine case. Accordingly, there are expressed forms of the human protein which correspond to the bVEGF$_{120}$ and bVEGF$_{164}$ proteins (however, since the human proteins contain an additional amino acid at position 7 not found in the bovine forms of vascular endothelial cell growth factor, the human forms of vascular endothelial cell growth factor contain 121 and 165 residues, respectively). A cDNA clone containing a portion of the coding region for hVEGF$_{121}$, designated λH3, has been deposited with the American Type Culture Collection with accession number 40728. A cDNA clone containing a portion of the coding region for hVEGF$_{165}$, designated λH2, has also been deposited with accession number 40727. Further clones can be obtained in an analogous fashion encoding the entire primary translation products for hVEGF$_{121}$ and hVEGF$_{165}$.

Based on composite sequence information obtained from the deposited human genomic clone of Example 5 and several cDNA clones obtained by the procedure described in Example 6, the native DNA coding sequences for hVEGF$_{121}$ and hVEGF$_{165}$ were determined. The DNA sequences are shown in FIG. 7. The boxed sequence of 132 nucleotides comprises the DNA sequence corresponding to the alternatively spliced portion of the message. When this sequence is present in the translated message, the encoded protein is hVEGF$_{165}$, the amino acid sequence of which is given directly above the nucleotide sequence of FIG. 7. When this sequence is not present in the translated message, the encoded protein is hVEGF$_{121}$. This form of the protein has the same amino acid sequence as hVEGF$_{165}$ through position 114. The carboxylterminal sequence of hVEGF$_{121}$, beginning at position 112, is shown in italics below the nucleotide sequence in FIG. 7. Contiguous cDNA sequences encoding hVEGF$_{121}$ and hVEGF$_{165}$ can be generated from synthetic oligonucleotides, or through the use of polymerase chain reactions from human fetal vascular smooth muscle poly(A)+ RNA, using methods analogous to those described in Example 4.

EXAMPLE 8

Expression of Polypeptides Having Amino Acid Sequences of Forms of Human Vascular Endothelial Cell Growth Factor A cDNA clone containing the entire coding region for the primary translation product of human vascular endothelial cell growth factor (hVEGF$_{121}$ or hVEGF$_{165}$) is most conveniently used in complete or truncated (modified) form to produce the recombinant protein in a variety of hosts as set forth in *Standard Procedures* above. However, expression in mammalian systems is favored as the host is capable of post translational processing analogous to that experienced by the natively produced protein, and either cDNA or genomic sequences may be used, as the host is also capable of processing introns.

Thus, a cDNA or genomic clone containing the entire coding region for either form of human vascular endothelial cell growth factor is prepared for insertion into a host vector, illustrated by, but not limited to, those described below.

To construct the vectors, the cloned cDNA or genomic insert is excised from the cloning vector in which it was isolated. The insert is provided with NcoI, BamHI, EcoRI or other appropriate linkers if necessary, and then inserted into an appropriate host vector such as pHS1 or its derivatives as described below. Alternatively, in vitro mutagenesis may be used to introduce convenient restriction sites or additional coding sequences into the cloned insert, before excision of the insert and insertion into an appropriate vector.

CONSTRUCTION OF HOST VECTORS pHS1

The plasmid pHS1 is suitable for expression of inserted DNA in mammalian hosts. It contains approximately 840 base pair of the human metallothionein-II$_A$ (hMT-IIA) sequence from p84H (Karin, M., et al., *Nature* (1982) 299:797–802) which spans from the HindIII site at position −765 of the hMT-II$_A$ gene to the BamHI cleavage site at base +70. To construct pHS1, plasmid p84H was digested to completion with BamHI, treated with exonuclease BAL-31 to remove terminal nucleotides, and then digested with HindIII. The desired approximately 840 base pair fragment was ligated into pUC8 (Vieira, J., et al., *Gene* (1982) 19:259–268) which had been opened with HindIII and HincII digestion. The ligation mixture was used to transform $E.\ coli$ HB101 to Amp$^R$, and one candidate plasmid, designated pHS1, was isolated and sequenced by dideoxy sequencing. pHS1 contains the hMT-II$_A$ control sequences upstream of a polylinker containing convenient restriction sites (BamHI, SmaI, and EcoRI).

The workable host plasmid pHS1 can be further modified to contain additional control elements besides the metallothionein promoter. In particular, the enhancer elements of viral systems, such as SV40, can be included, as well as termination signals associated with the 3' untranslated regions of other proteins such as human growth hormone (hGH).

VIRAL ENHANCER

A pair of host expression vectors containing the SV40 enhancer in operable linkage to the MT-II$_A$ promoter was constructed by inserting an 1118 base pair SV40 DNA fragment into the HindIII site preceding the MT-II$_A$ promoter sequences of pHS1. The SV40 DNA fragment spans the SV40 origin of replication and includes nucleotide 5172 through nucleotide 5243 (at the origin), the duplicated 72 base pair repeat from nucleotide 107-250, and continues through nucleotide 1046 on the side of the origin containing the 5' end of late viral genes. This HindIII 1118 base pair fragment is obtained from a HindIII digest of SV40 DNA (Buchman, A. R., et al., *DNA Tumor Viruses*, 2nd ed (J. Tooze, ed.), Cold Spring Harbor Laboratory, New York (1981), pp. 799-841), and cloned into pBR322 for amplification. The pBR322 vector containing the SV40 fragment was cut with HindIII, and the 1118 base pair SV40 DNA fragment was isolated by gel electrophoresis and ligated into HindIII-digested, CIP-treated, pHS1. The resulting vectors, designated pHS1-SV(9) and pHS1-SV(10), contain the SV40 fragment in opposite orientation preceding the MT-II$_A$ promoter. In pHS1-SV(9), the enhancer is about 1600 base pair from the 5' mRNA start site of the MT-II$_A$ promoter, in the opposite orientation it is approximately 980 base pair from the 5' mRNA start site. Both orientations are operable, but the orientation wherein the enhancer sequences are proximal to the start site provides higher levels of expression. It is believed that deletions which place the enhancer 250-400 base pairs upstream of the transcription start are optimal.

Additional vectors were constructed which place the SV40 enhancer 3' terminus 190 base pairs, 250 base pairs, and 360 base pairs respectively upstream from the 5' end of the MT-II$_A$ promoter TATA box. The constructions were based on the mapping of the upstream regulatory regions of the human MT-II$_A$ promoter described by Karin, M., et al., *Nature* (1984) 308:513-519. All constructions retain the sequences containing the duplicated sites for regulation by heavy metals, but the constructions with the 190 base pair and 250 base pair separations do not retain the sequence for glucocorticoid regulation which is further upstream from these heavy metal regulatory sites.

These vectors, designated pHS'-SV190, pHS'-SV250, and pHS'-SV360 are prepared as outlined below. All constructions are identical except for the length of sequence containing the metallothionein promoter and upstream region which is supplied as a fragment excised from pHS1.

For pHS'-SV190, pHS1 is digested with SacII, blunted, and ligated to KpnI linkers. The DNA is then digested with EcoRI and KpnI to liberate the appropriate portion of the MT-II$_A$ control sequences. Similarly, for pHS'-SV250, pHS1is digested with HgaI, blunted, ligated to KpnI linkers and digested with EcoRI and KpnI; for pHS'-SV360, DdeI is used in the initial digestion.

An intermediate vector containing the SV40 enhancer is prepared by inserting the HindIII/KpnI fragment of SV40 (which extends from position 5172 to position 298 and which contains the enhancer element 50 base pairs from the KpnI site) into KpnI/HindIII digested pUC19 to obtain pUC-SV. (pUC19 contains three convenient restriction sites in the polylinker region, in order, HindIII, KpnI, and EcoRI.) The finished vectors are obtained by inserting the KpnI/EcoRI fragments prepared as described above into KpnI/EcoRI digested pUC-SV.

All of the foregoing modified vectors, thus, take advantage of the SV40 enhancer element. Other viral enhancers could, of course, be used in an analogous manner.

TRANSCRIPTION TERMINATION SEQUENCES

To provide transcription termination control sequences, DNA representing the coding sequence and 3' untranslated sequence of human growth hormone was ligated into pHS1. The intermediate vector can provide the hGH 3' untranslated sequence to coding sequences subsequently ligated into the vector in place of the hGH coding sequence.

The genomic sequences encoding hGH were isolated from p2.6-3 (DeNoto, et al., *Nucleic Acids Res.* (1981) 19:3719) by digestion with BamHI, which cuts at the 5' end of the first exon, and EcoRI, which cuts 3' of the functional gene, followed by polyacrylamide gel purification. The isolated fragment was ligated into BamHI/EcoRI digested pHS1 and the ligation mixture transformed into *E. coli* MC1061 to Amp ®. Successful transformants were screened by restriction analysis, and a strain containing the desired plasmid, pMT-hGHg, was further propagated to prepare quantities of plasmid DNA.

In a manner similar to that described above for construction pHS1-SV(9) or pHS1-SV(10), but substituting for pHS1, pMT-hGHg, a pair of vectors containing the hGH gene under the control of the MT-II$_A$ promoter, and operably linked to the SV40 enhancer, and designated, respectively, phGHg-SV(9) and phGHg-SV(10), were obtained. The ligation mixtures were used to transform *E. coli* MC1061 to Amp ®, and the correct constructions verified.

CONSTRUCTION OF EXPRESSION VECTORS phGHg-SV(10) is used as a host vector to accommodate human vascular endothelial cell growth factor. phGHg-SV(10) is digested with BamHI and SmaI, blunted with Klenow, and treated with CIP to excise the hGH coding sequence. This opened vector is ligated to the insert fragment derived from a cDNA or genomic clone encoding fulllength vascular endothelial cell growth factor to obtain expression vector pVEGF-SV(10).

It is envisioned that the full primary translation product of the vascular endothelial cell growth factor gene will contain a secretion signal sequence. If not, synthetic oligonucleotides can be added to the vascular endothelial cell growth factor insert to operably join a heterologous secretion signal sequence (e.g. from hGH) to the vascular endothelial cell growth factor produced. In either case, secretion of the product should result.

In addition, other host vectors may be used to obtain expression of the vascular endothelial cell growth factor gene or cDNA sequences, including pHS1and pHS1 modified to contain the various configurations of SV40 enhancer as above described. Finally, the host vectors may be further modified such that they encode not only vascular endothelial cell growth factor, but the neomycin resistance gene (obtained from pSV2:NEO) and/or the human metallothionein-II$_A$ protein as well (called pMT-VEGF-NEO or pMT-VEGF-NEO-MT).

These vectors are generically designated pMT-VEGF for the purposes of the discussion below.

PRODUCTION OF VASCULAR ENDOTHELIAL CELL GROWTH FACTOR BY MAMMALIAN RECOMBINANTS

Chinese hamster ovary (CHO)-K1 cells are grown in medium composed of a 1:1 mixture of F12 medium and DME medium with 12% fetal calf serum. The competent cells are co-transformed with pMT-VEGF and pSV2:NEO (Southern, P., et al., *J. Mol. Appl. Genet.* (1982) 1:327-341), pSV2:NEO contains a functional gene conferring resistance to the neomycin analog G418. In the transformation, 1 μg of pSV2:NEO and 10 μg of pMT-VEGF are applied to cells in a calcium phosphate-DNA co-precipitate according to the protocol of Wigler, M., et al., *Cell* (1979) 16:777-785, with the inclusion of a two minute "shock" with 15% glycerol after four hours of exposure to the DNA. Alternatively, the cells can be transformed with 10 μg pMT-VEGF-NEO or pMT-VEGF-NEO-MT, using the same calcium phosphate protocol. A day later, the cells are subjected to 1 mg/ml G418 to provide a pool of G418-resistant colonies. After sufficient growth of the pool of resistant colonies, the pool is assayed for vascular endothelial cell growth factor production in either cell-associated or secreted form.

Successful G418-resistant transformants, also having a stable inheritance of pMT-VEGF, or other vascular endothelial cell growth factor expression plasmid, are plated at low density for purification of clonal isolates. Small amounts of these isolates are grown in multi-well plates after exposure to $2 \times 10^{-4}$ M zinc chloride for convenient assay of vascular endothelial cell growth factor production. Vascular endothelial cell growth factor determinations are made by mitogenic assays testing endothelial cell mitogenic activity present in the cells and/or conditioned medium, or by standard ELISA or radioimmunoassays against the antisera prepared against the appropriate vascular endothelial cell growth factor protein or peptides using standard methods. Clonal isolates which produce large amounts of the desired vascular endothelial cell growth factor, preferably in secreted form, are selected.

The cells are seeded at 1/10 confluency in basal medium (1:1 mix of F12 medium and DME medium) supplemented with 10% fetal calf serum, incubated overnight, and then induced for vascular endothelial cell growth factor production by addition of zinc chloride in the concentration range of $1 \times 10^{-4}$M to $3 \times 10^{4}$M.

In another method for establishing vascular endothelial cell growth factor cells, CHO cells are cotransformed with pMT-VEGF, pSV:NEO, and pHS1containing a human MT-II$_A$ insert (pHS1-MT) or with pMT-VEGF-NEO-MT. After G418 selection, pooled resistant colonies are selected for cadmium resistance (due to expression of MT-II$_A$ protein) by growing them in the presence of 10 μM CdCl$_2$ with 100 μM ZnCl$_2$ as inducer. Pools of resistance clones are then assayed, as described above, to measure vascular endothelial cell growth factor production levels.

Purification of the secreted vascular endothelial cell growth factor can then be carried out according to the procedures set forth in Example 9, or by other standard methods known in the art.

By including in the expression vector construction an operable secretion signal sequence for vascular endothelial cell growth factor, such as the native vascular endothelial cell growth factor signal or the signal derived from hGH, secretion using the normal constitutive pathways could be effected using CHO or other mammalian cell hosts. Effecting secretion has some advantages, of course, since the protein purification task becomes much simpler, and folding of the protein may be closer to the native configuration, eliminating the need for refolding steps. Purification of the secreted vascular endothelial cell growth factor can then be carried out according to the procedures set forth in Example 9, or by other standard methods known in the art.

EXAMPLE 9

Recovery of Polypeptide and Formation of Dimeric Vascular Endothelial Cell Growth Factor When expressed in a mammalian expression system in such a way as to obtain secretion of the produced growth factor, the vascular endothelial cell growth factor (e.g. hVEGF$_{121}$ or hVEGF$_{165}$) can be purified by the procedure of Gospodarowicz, et al., *PNAS* (1989) 86(19):7311-7315. The medium conditioned by the host cells expressing the growth factor is centrifuged at 10000 g for 15 to 30 minutes. The supernatant solution is adjusted to pH 5 to 6 with 1 N HCl, and at least 500 g of ammonium sulfate is added per liter. The solution is stirred for 2 to 6 hours at 4° C. and then centrifuged for 30 to 60 minutes at 10000 g. The supernatant is discarded, and the pellet is retained for further purification.

The pellet is redissolved in 5 to 25 mM Tris, pH 6.5 to 8.0, containing 25 to 100 mM NaCl. The solution is dialysed overnight against the same buffer. Any precipitated material is centrifuged out of solution and discarded (10000 g, 30 to 60 minutes). The solution is loaded onto a column of heparin-Sepharose, which is equilibrated with the same buffer used for dialysis. After all of the protein solution is loaded, the column is washed with the equilibration buffer until the eluant absorbance returns to baseline levels. The protein is step-eluted from the column with equilibration buffer containing between 0.1M and 2.5M NaCl. Active fractions are combined and concentrated in an Amicon stirred cell with a 10,000 MW cutoff membrane.

The concentrated biologically active material which is collected from the heparin-Sepharose column is applied to a column of Bio-Gel P—60 equilibrated in phosphate buffered saline. The column is eluted in the same buffer and the biologically active fractions are combined. This material is diluted three fold with 20 mM HEPES pH 8.3 and loaded onto a Mono-S column. The column is eluted with a gradient of 0.0M to 1.0M NaCl in the same buffer. For structural studies, the final purification is accomplished on a Vydac C4 reverse phase column (RP-HPLC) with a gradient of 10 to 60% acetonitrile in water containing 0.1% trifluoroacetic acid.

When a bacterial expression system is used to produce the protein in inclusion bodies, the product is purified in a manner analogous to the method of Hoppe, et al., *Biochemistry* (1989) 28:2956-2960. The cells are suspended in 5 to 25 mM Tris pH 6.5 to 8.0, 1 mM EDTA and are ruptured by passage through a microfluidizer. The solution is centrifuged at 10000 g for 15 to 30 minutes and the pellet is washed with 5 to 25 mM Tris pH 6.5 to 8.0, 1 mM EDTA and 1 to 2% Triton X—100.

The pellet is resuspended in 20 mM Tris pH 7.5, 1 mM EDTA, 6M guanidine-HCl, 0.1M Na$_2$SO$_3$, and 0.01 mM Na$_2$S$_4$O$_6$, and the solution is left at room temperature for 4 to 12 hours. This step converts the molecule to the monomeric form. Insoluble material is removed by centrifugation.

The resulting S-sulfonated protein is chromatographed on Sephacryl S-200 equilibrated in 10 to 50 mM Tris pH 6.5 to 8.0, 1 mM EDTA, 3 to 6M guanidine-HCl. Those fractions containing the protein are pooled and are dialysed against water. Final purification of the S-sulfonated protein is accomplished on RP-HPLC C4 chromatography. The protein is eluted with a linear gradient of 0% to 100% acetonitrile (chamber A for making the gradient is 0.1% trifluoroacetic acid in water and chamber B is 0.1% trifluoroacetic acid in acetonitrile).

The protein is dissolved to a final concentration of 0.1 to 0.5 mg/ml in 50 mM Tris pH 8.0, 1 mM EDTA, 5 mM glutathione and 0.5 mM glutathione disulfide with enough urea to maintain solubility of the protein. At this step the protein folds to form the native homodimeric structure of vascular endothelial cell growth factor. After two days the protein is repurified on same RP-HPLC system as above, or by affinity chromatography steps such as heparin-Sepharose or Mono-S. Monomers are separated from dimers by chromatography on S-Sepharose in 20 mM Tris-HCl, pH 7.5; the dimers are eluted from the column with 20 mM Tris, pH 7.5 containing 0.7M NaCl.

EXAMPLE 10

Wound Healing Formulations Containing Vascular Endothelial Cell Growth Factor

A parenteral solution suitable for administration intravascularly via catheter to a wound site can be prepared by dissolving vascular endothelial cell growth factor (e.g. bVEGF$_{120}$, bVEGF$_{164}$, hVEGF$_{121}$ or hVEGF$_{165}$) in water for injection, together with a suitable amount of buffer to maintain stable pH in the range of 5.0 to 7.0 and a suitable amount of sodium chloride to attain isotonicity. A typical composition is as follows:

|  | mg/ml |
| --- | --- |
| Vascular endothelial cell growth factor | 0.05–1.0 |
| Citric acid | 0.2 |
| Sodium chloride | 8.5 |

0.01 N sodium hydroxide to adjust pH to 6.0
Water for injection sufficient to make 1.0 ml.

The solution described above can also be applied topically to a wound site with the assistance of a mechanical spray pump.

An aqueous gel, suitable for topical application to a wound site, can be prepared by dispersing the thickening agent hydroxyethylcellulose (250H grade) in an aqueous solution containing buffer, preservative and tonicity modifier. When the thickening agent is completely dissolved, a concentrated aqueous solution of vascular endothelial cell growth factor is added and mixed until the product is uniform. The following pharmaceutical composition is typical of such a gel:

|  | mg/ml |
| --- | --- |
| Vascular endothelial cell growth factor | 0.05–1.0 |
| Hydroxyethylcellulose (250H) | 20 |

-continued

|  | mg/ml |
| --- | --- |
| Chlorhexidine gluconate | 2.5 |
| Citric acid | 0.5 |
| Glycerin | 20 |

0.01N sodium hydroxide to adjust pH to 6.0.
Purified water sufficient to make 1 ml.

A dry powder, suitable for dusting onto a wound site, can be prepared by lyophilizing vascular endothelial cell growth factor with a water soluble carrier and comminuting the lyophilized product to yield a powder of uniform particle size. The powder can be applied to the wound site directly or with the aid of an aerosol propellant. A typical powder composition is prepared as follows:

|  | mg/ml |
| --- | --- |
| Vascular endothelial cell growth factor | 0.05–1.0 |
| Dextran (Mol. wt. 1000) | 100 |

Purified water sufficient to make 1 ml

The solution is freeze dried and the resulting dried substance is ground in a ball mill to a medium particle size of about 75 μm. The powder can be applied by a shaker. In case a large surface area needs to be covered, the powder can be delivered by an aerosol-driven canister containing fluorocarbon (Freon®), hydrocarbon (isobutane) or compressed gas (carbon dioxide) as the propellant.

EXAMPLE 11

Preparation of Chimeric Growth Factor

A chimeric molecule containing one chain of vascular endothelial cell growth factor and one A chain of platelet-derived growth factor is prepared by first constructing vectors for the recombinant expression of these two molecules. Expression vectors to direct the synthesis of human vascular endothelial cell growth factor in mammalian cells are described in Example 8. The preferred vector is one that is constructed such that the synthesized vascular endothelial cell growth factor is secreted from the host cell (e.g , phGHg-SV(10), altered such that the coding region for the full primary translation product of vascular endothelial cell growth factor, including the native vascular endothelial cell growth factor secretion signal, is operably inserted between the BamHI and SmaI sites of the parental vector). A similar vector is constructed for the expression of the A chain of platelet-derived growth factor by taking a synthetic or partially-synthetic DNA fragment having the sequence shown in FIG. 4a (which encodes the full primary translation product of the A chain), digesting with BamHI and EcoRV, and inserting the resulting coding region fragment between the BamHI and SmaI sites of phGHg-SV(10).

For production of the growth factor chains, the expression plasmids are introduced into mammalian hosts cells, such as CHO cells, by the calcium phosphate precipitation method described in Example 8. Two different transformations of the CHO cells are carried out: in one transformation, the DNA introduced into the cells represents a co-transformation of the vascular endothelial cell growth factor expression plasmid and pSV2:NEO in a 10:1 weight ratio; in the other transformation, the co-transformation is with the platelet-derived growth factor A-chain expression vector and pSV2:NEO in a 10:1 weight ratio. G418-resistant pools of transformants are selected from each transformation, and individual growth factor-producing clones are screened for high-level growth factor production by assays of the conditioned medium for mitogenic activity on endothelial cells (in the case of vascular endothelial cell growth factor-producing cells) or on mouse NIH 3T3 cells obtainable from the ATCC (#ATCC CRL 1658) (in the case of platelet-derived growth factor A-chain-producing cells), or by ELISA or radio-immune assays for the two growth factor chains developed by methods standard in the art.

In an alternative approach, a transformation is carried out in which three plasmids are co-precipitated with calcium phosphate onto the cells: the expression vector for vascular endothelial cell growth factor, the expression vector for platelet-derived growth factor A-chain, and pSV2:NEO (in a weight ratio of 10:10:1). A G418-resistant pool of clones is selected from the transformation, and individual clones are then screened by ELISA or other antibody-based assays for the simultaneous secretion of both of the growth factor chains.

Purification of the vascular endothelial cell growth factor chains from conditioned medium is carried out as described in Example 9. Purification of the platelet-derived growth factor A-chains from conditioned medium is carried out following the protocols known in the art, e.g., the protocol of Heldin, et al., *Nature* (1986) 319:511–514. In this latter protocol, the conditioned medium containing the secreted growth factor is fractionated by adsorption to Sulphadex beads, followed by elution of the platelet-derived growth factor A-chain material with 1.5M NaCl in 0.01M phosphate buffer, pH 7.4. After ammonium sulphate precipitation to concentrate the eluted protein, the sample is resuspended in 1M NaCl, 0.01M phosphate buffer, pH 7.4, and dialyzed against this buffer. The sample is then fractionated over a Sephacryl S−200 column (elution with 1M NaCl, 0.01M phosphate buffer, pH 7.4), dialyzed against 1M acetic acid, lyophilized, dissolved in 1M acetic acid, and applied to a BioGel P−150 column (elution with 1M acetic acid). After lyophilization of the fractions containing the A-chain material, the sample is re-dissolved in 1M acetic acid and fractionated by reverse-phase HPLC (elution with a gradient of 0 to 50% propanol in 1M acetic acid, 2M guanidine-HCl).

A chimeric dimer containing one chain of vascular endothelial cell growth factor and one chain of platelet-derived growth factor A-chain is produced by mixing the two purified samples of these proteins prepared as described above. The mixture is then denatured and refolded as described in Example 9. Briefly, the mixture is first denatured and S-sulfonated by treatment with 20 mM Tris, pH 7.5, 1 mM EDTA, 6M guanidine-HCl, 0.1M $Na_2SO_3$, 0.01 mM $Na_2S_4O_6$ for 4 to 12 hours at room temperature. After fractionation over Sephacryl S−200 and purification by reverse-phase HPLC (see Example 9), the S-sulfonated chains are lyophilized and then dissolved at a final concentration of 0.1 to 0.5 mg/ml in 50 mM Tris-HCl, pH 8.0, 1 mM EDTA, 5 mM glutathione, 0.5 mM glutathione disulfide with enough urea to maintain solubility of the protein chains. Monomers are separated from dimers by chromatography on S-Sepharose in 20 mM Tris-HCl, pH 7.5, using steps of increasing concentrations of NaCl in the Tris buffer for elution. The chimeric dimers are then separated from the homodimers by a combination of the steps used to purify the individual homodimers before the denaturation and refolding steps were carried out. Additionally, the chimeric molecule can be purified by passage over an anti-vascular endothelial cell growth factor antibody column, followed by passage over an anti-platelet-derived growth factor A-chain antibody column, following procedures known in the art.

We claim:

1. Isolated vascular endothelial cell growth factor selected from the group consisting of bovine vascular endothelial cell growth factor of 120 amino acids and human vascular endothelial cell growth factor of 121 amino acids.

2. Isolated human vascular endothelial cell growth factor of 121 amino acids.

* * * * *